United States Patent
Nishimura et al.

(10) Patent No.: US 9,770,498 B2
(45) Date of Patent: Sep. 26, 2017

(54) IMP-3 EPITOPE PEPTIDES FOR TH1 CELLS AND VACCINES CONTAINING THE SAME

(71) Applicant: OncoTherapy Science, Inc., Kanagawa (JP)

(72) Inventors: Yasuharu Nishimura, Kumamoto (JP); Yusuke Tomita, Kumamoto (JP); Masatoshi Hirayama, Kumamoto (JP); Ryuji Osawa, Kawasaki (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 14/890,146

(22) PCT Filed: May 22, 2014

(86) PCT No.: PCT/JP2014/002678
§ 371 (c)(1),
(2) Date: Nov. 9, 2015

(87) PCT Pub. No.: WO2014/188721
PCT Pub. Date: Nov. 27, 2014

(65) Prior Publication Data
US 2016/0114018 A1   Apr. 28, 2016

(30) Foreign Application Priority Data

May 24, 2013 (JP) .................................. 2013-109567

(51) Int. Cl.
| | | |
|---|---|---|
| A61K 38/00 | (2006.01) | |
| A61K 39/00 | (2006.01) | |
| A61K 31/7088 | (2006.01) | |
| C07K 14/65 | (2006.01) | |
| A61K 35/17 | (2015.01) | |
| A61K 35/26 | (2015.01) | |

(52) U.S. Cl.
CPC ...... *A61K 39/0011* (2013.01); *A61K 31/7088* (2013.01); *A61K 35/17* (2013.01); *C07K 14/65* (2013.01); *A61K 35/26* (2013.01); *A61K 38/00* (2013.01); *A61K 2039/55566* (2013.01); *A61K 2039/57* (2013.01); *A61K 2039/572* (2013.01); *A61K 2039/585* (2013.01)

(58) Field of Classification Search
None
See application file for complete search history.

(56) References Cited

U.S. PATENT DOCUMENTS

| | | | |
|---|---|---|---|
| 7,258,860 B2 * | 8/2007 | Wang ................ | A61K 39/0011 424/184.1 |
| 7,700,573 B2 | 4/2010 | Nakamura et al. | |
| 7,847,060 B2 | 12/2010 | Tahara et al. | |
| 7,972,772 B2 | 7/2011 | Nakamura et al. | |
| 8,053,183 B2 | 11/2011 | Nakamura et al. | |
| 8,614,176 B2 | 12/2013 | Tahara et al. | |
| 8,771,963 B2 | 7/2014 | Nakamura et al. | |
| 2006/0024692 A1 | 2/2006 | Nakamura et al. | |
| 2009/0317392 A1 | 12/2009 | Nakamura et al. | |
| 2011/0223687 A1 | 9/2011 | Nakamura et al. | |
| 2012/0308590 A1 | 12/2012 | Nishimura et al. | |

FOREIGN PATENT DOCUMENTS

| | | | |
|---|---|---|---|
| WO | 03/061681 | * | 7/2003 |
| WO | 2004/031413 A2 | | 4/2004 |
| WO | 2005/090603 A2 | | 9/2005 |
| WO | 2006/090810 A2 | | 8/2006 |
| WO | 2007/013665 A2 | | 2/2007 |
| WO | 2007/013671 A2 | | 2/2007 |
| WO | 2007/097469 A1 | | 8/2007 |
| WO | 2011/067920 A1 | | 6/2011 |

OTHER PUBLICATIONS

Engelhard, Current Opinion in Immunology vol. 6 p. 13 (1994).*
Guo, et al Nature vol. 360 p. 384 (1992).*
Rammensee et al, Immunogenetics vol. 41 p. 178 (1995).*
Shastri et al J. Immunol. 1995 vol. 155 p. 4339.*
International Search Report of International Patent Application No. PCT/JP2014/002678, 6 pages, (2014).
Belli, et al., "Vaccination of Metastatic Melanoma Patients With Autologous Tumor-Derived Heat Shock Protein gp96-Peptide Complexes: Clinical and Immunologic Findings," *J Clin Oncol.*, vol. 20(20), pp. 4169-4180 (Oct. 15, 2002).
Bevan, "Helping the CD8+ T-Cell Response," *Nat Rev Immunol.*, vol. 4 (8), pp. 595-602 (Aug. 2004).
Boon, "Tumor Antigens Recognized by Cytolytic T Lymphocytes: Present Perspectives for Specific Immunotherapy," *Int J Cancer.* vol. 54(2), pp. 177-180 (May 8, 1993).
Boon, et al., "Human Tumor Antigens Recognized by T Lymphocytes," *J Exp Med.*, vol. 183(3), pp. 725-729 (Mar. 1, 1996).
Bos, et al., "CD4+ T-Cell Help in the Tumor Milieu is Required for Recruitment and Cytolytic Function of CD8+ T Lymphocytes," *Cancer Res.*, vol. 70(21), pp. 8368-8377 (Nov. 2010).
Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).
Chamoto, et al., "Potentiation of Tumor Eradication by Adoptive Immunotherapy with T-cell Receptor Gene-Transduced T-Helper Type 1 Cells," *Cancer Res.*, vol. 64 (1), pp. 386-390 (Jan. 2004).

(Continued)

*Primary Examiner* — Sheela J Huff
(74) *Attorney, Agent, or Firm* — Kilpatrick Townsend & Stockton LLP

(57) ABSTRACT

Isolated IMP-3-derived epitope peptides having Th1 cell inducibility are disclosed herein. Such peptides can be recognized by MHC class II molecules and induce Th1 cells. The peptides of the present invention can promiscuously bind to MHC class II molecules and induce IMP-3-specific cytotoxic T lymphocytes (CTLs) in addition to Th1 cells. Such peptides are thus suitable for use in enhancing immune response in a subject, and accordingly find use in cancer immunotherapy, in particular, as cancer vaccines. Also disclosed herein are polynucleotides that encode any of the aforementioned peptides, APCs and Th1 cells induced by such peptides and methods of induction associated therewith. Pharmaceutical compositions that comprise any of the aforementioned components as active ingredients find use in the treatment and/or prevention of cancers or tumors expressing IMP-3.

13 Claims, 7 Drawing Sheets

(56) References Cited

OTHER PUBLICATIONS

Coulie, et al., "Cytolytic T-cell responses of cancer patients vaccinated with a Mage antigen," *Immunol Rev.*, vol. 188, pp. 33-42 (Oct. 2002).

Fujie, et al., "A *MAGE*-1-Encoded HLA-A24-Binding Synthetic Peptide Induces Specific Anti-Tumor Cytotoxic T Lymphocytes," *Int J Cancer*, vol. 80(2), pp. 169-172 (Jan. 18, 1999).

Harris, "Structure and Function of the p53 Tumor Suppressor Gene: Clues for Rational Cancer Therapeutic Strategies," *J Natl Cancer Inst.* vol. 88(20), pp. 1442-1455 (Oct. 16, 1996).

Hirayama, et al., "Identification of a single tumor antigen peptide that can induce both Th cells and CTLs and is derived from oncofetal antigen IMP-3," Proceedings of the 17th annual meeting of Japanese Association of Cancer Immunology, Jun. 10, 2013, p. 79, 0S4-2, with English translation.

Hirayama, et al., "Identification of a promiscuous IMP-3-derived long peptide that can induce both Th cells and CTLs," Proceedings of Annual Meeting of the Japanese Society for Immunology, Nov. 18, 2013, vol. 42 p. 112, 2-B-W25-1-0/P.

Kikuchi, et al., "Identification of a SART-1-Derived Peptide Capable of Inducing HLA-A24-Restricted and Tumor-Specific Cytotoxic T Lymphocytes," *Int J Cancer*, vol. 81(3), pp. 459-466 (May 5, 1999).

Kono, et al., "Vaccination with multiple peptides derived from novel cancer-testis antigens can induce specific T-cell responses and clinical responses in advanced esophageal cancer," *Cancer Sci.*, vol. 100 (8), pp. 1502-1509 (Aug. 2009).

Kono, et al., "Multicenter, phase II clinical trial of cancer vaccination for advanced esophageal cancer with three peptides derived from novel cancer-testis antigens," *J Transl Med.*, vol. 10 (141), pp. 1-9 (Jul. 2012).

Melief, et al., "Immunotherapy of established (pre)malignant disease by synthetic long peptide vaccines," *Nat Rev Cancer.*, vol. 8(5), pp. 351-360 (May 2008).

Mizukami, et al., "Detection of novel cancer-testis antigen-specific T-cell responses in TIL, regional lymph nodes, and PBL in patients with esophageal squamous cell carcinoma," *Cancer Sci.* vol. 99(7), pp. 1448-1454 (Jul. 2008).

Oiso, et al., "A Newly Identified *MAGE*-3-Derived Epitope Recognized by HLA-A24-Restricted Cytotoxic T Lymphocytes," *Int J Cancer*, vol. 81(3), pp. 387-394 (May 5, 1999).

Rosenberg, et al., "Cancer immunotherapy: moving beyond current vaccines," *Nat Med.*, vol. 10(9), pp. 909-915 (Sep. 2004).

Shedlock, et al., "Requirement for CD4 T Cell Help in Generating Functional CD8 T Cell Memory," *Science*, vol. 300 (5617), pp. 337-339 (Apr. 2003).

Street, et al., "Perforin and interferon-γ activities independently control tumor initiation, growth, and metastasis," *Blood* vol. 97(1), pp. 192-197 (Jan. 2001).

Suda, et al., "Identification of human leukocyte antigen-A24-restricted epitope peptides derived from gene products upregulated in lung and esophageal cancers as novel targets for immunotherapy," *Cancer Sci.*, vol. 98(11), pp. 1803-1808 (Nov. 2007).

Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).

Tomita, et al., "Peptides derived from human insulin-like growth factor-II mRNA binding protein 3 can induce human leukocyte antigen-A2-restricted cytotoxic T lymphocytes reactive to cancer cells," *Cancer Sci.*, vol. 102(1), pp. 71-78 (Jan. 2011).

Tomita, et al., "Development of an Ideal and Potent Cancer Immunotherapy Designed by Consideration of HLA Polymorphism," *Major Histocompatibility Complex* [online], vol. 20(1), pp. 45-56 (Mar. 26, 2013), with English translation.

Van Der Burg, et al., "Immunogenicity of Peptides Bound to MHC Class 1 Molecules Depends on the MHC-Peptide Complex Stability," *J Immunol.*, vol. 156(9), pp. 3308-3314 (May 1, 1996).

Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).

Hirayama et al., "An Oncofetal Antigen, IMP-3-Derived Long Peptides Induce Immune Responses of Both Helper T Cells and CTLs," Oncoimmunology, 2016, vol. 5, No. 6, e1123368, 14 pages.

U.S. Appl. No. 15/501,125, submitted Feb. 1, 2017, 122 pages.

\* cited by examiner

[Fig. 1]
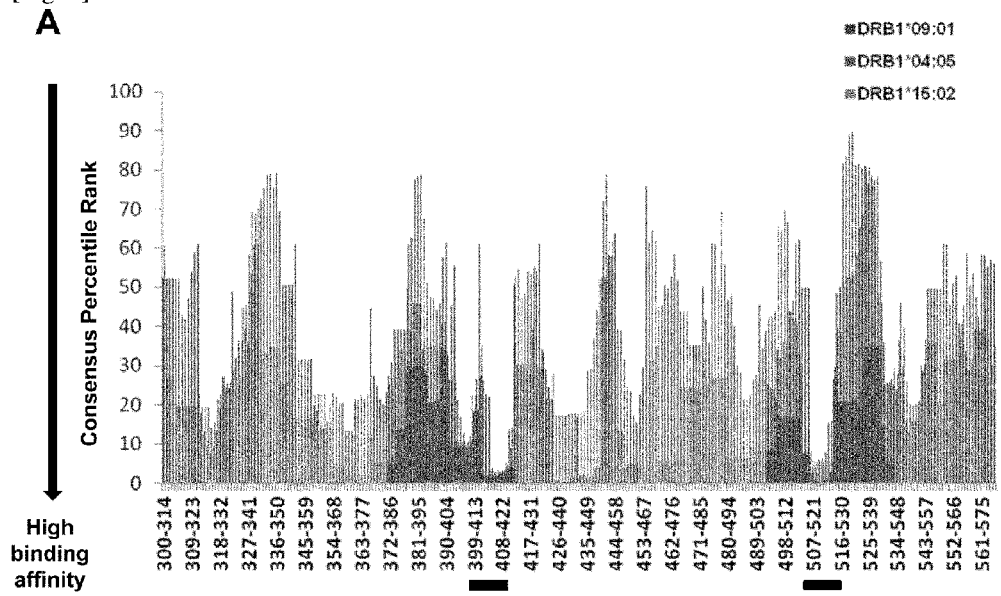
B
1. IMP-3$_{402-423}$-LP: (QSETETVHLFIPALSVGAIIGK)  22mer (SEQ ID NO: 1)
2. IMP-3$_{507-527}$-LP: (GKTVNELQNLSSAEVVVPRDQ)  21mer (SEQ ID NO: 2)
   IMP-3-A24$_{508-516}$  IMP-3-A2$_{515-523}$

[Fig. 2A-B]
A 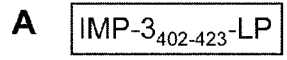
HD1: *DRB1\*04:05/-, DRB4\*01:03* (DR53)
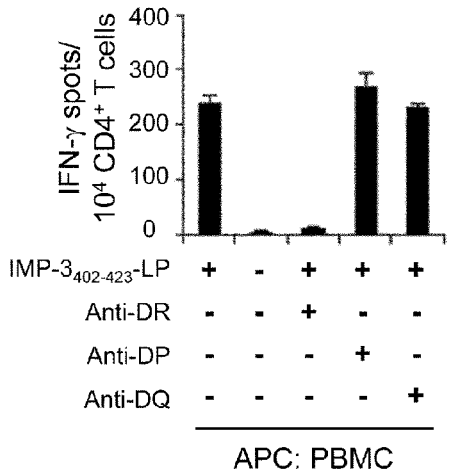
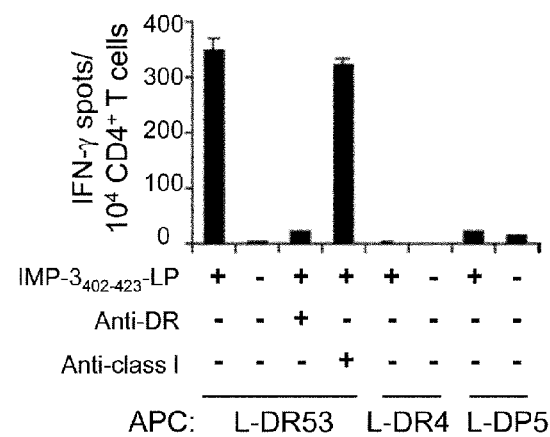
B 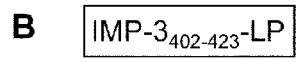
HD2: *DRB1\*0803/15:02*
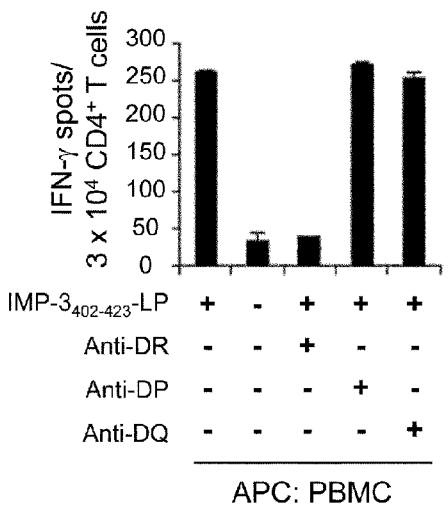

[Fig. 2C-E]
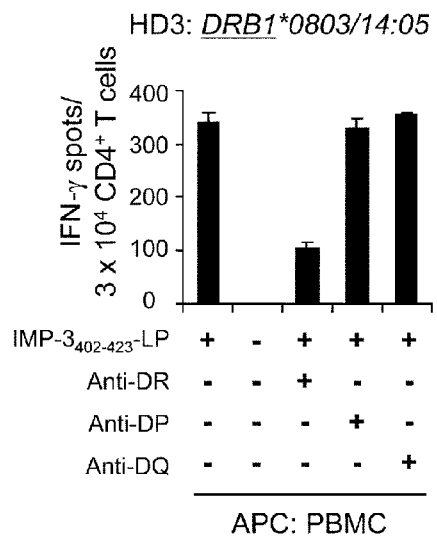
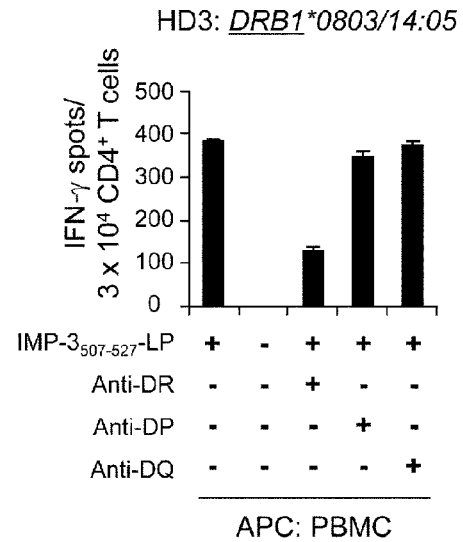
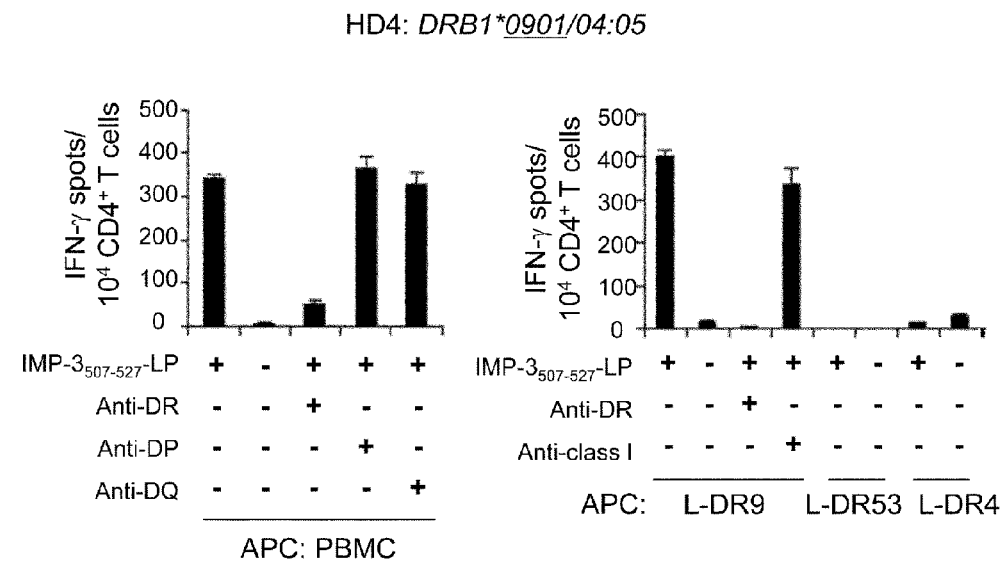

[Fig. 3]
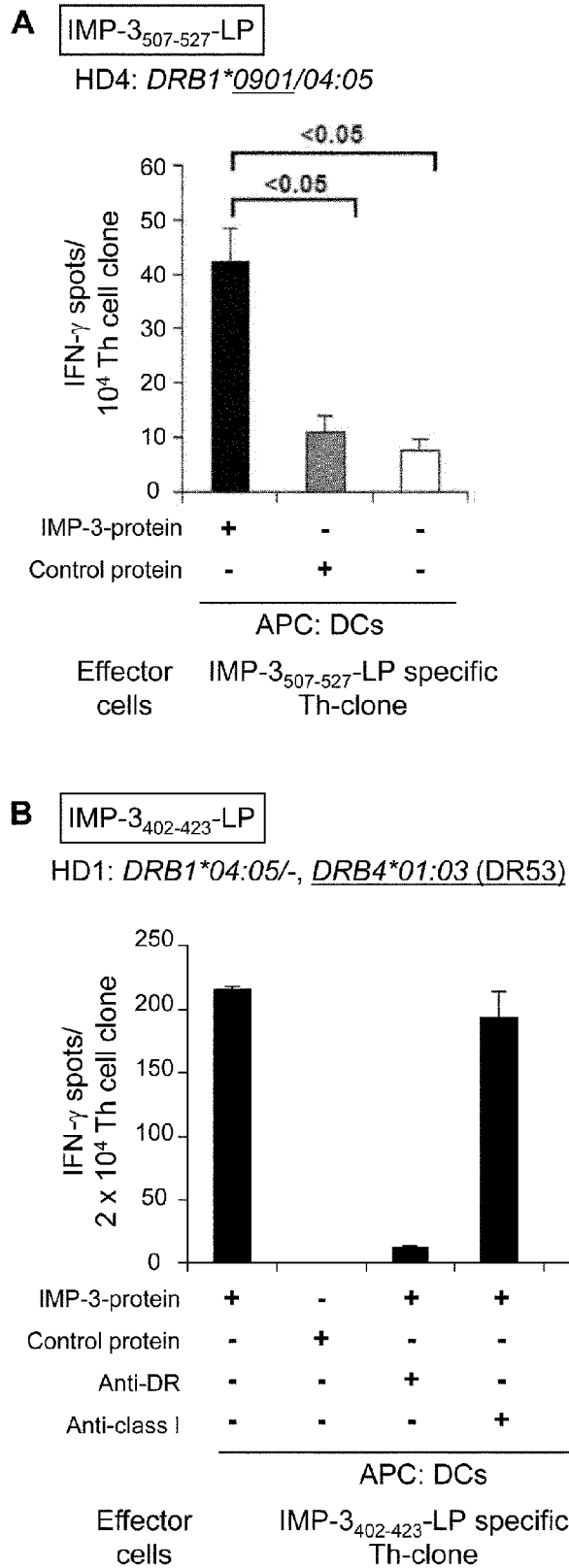

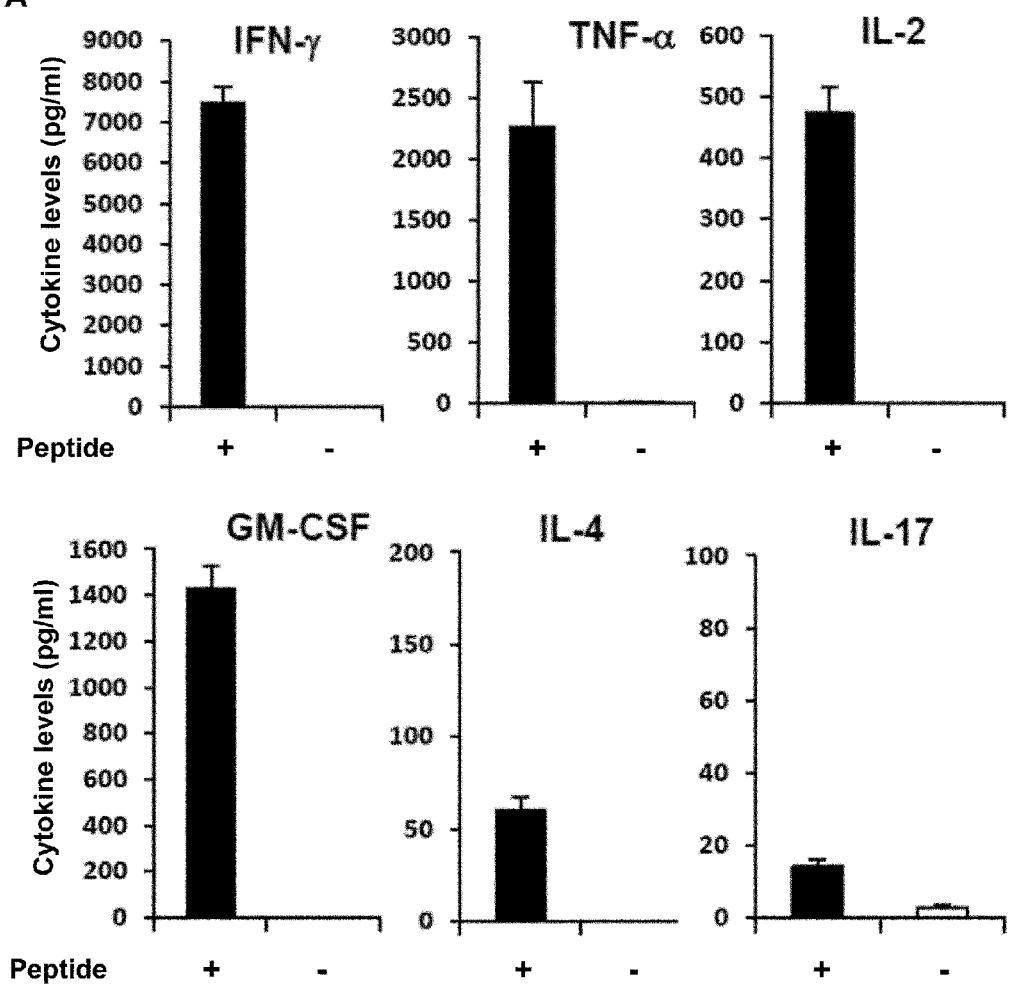
[Fig. 4A]

[Fig. 4B]
B
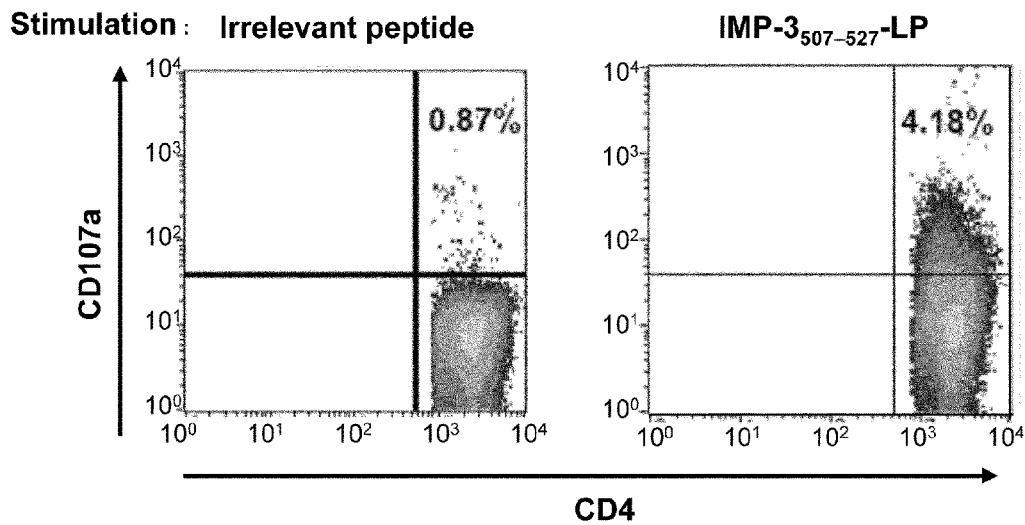
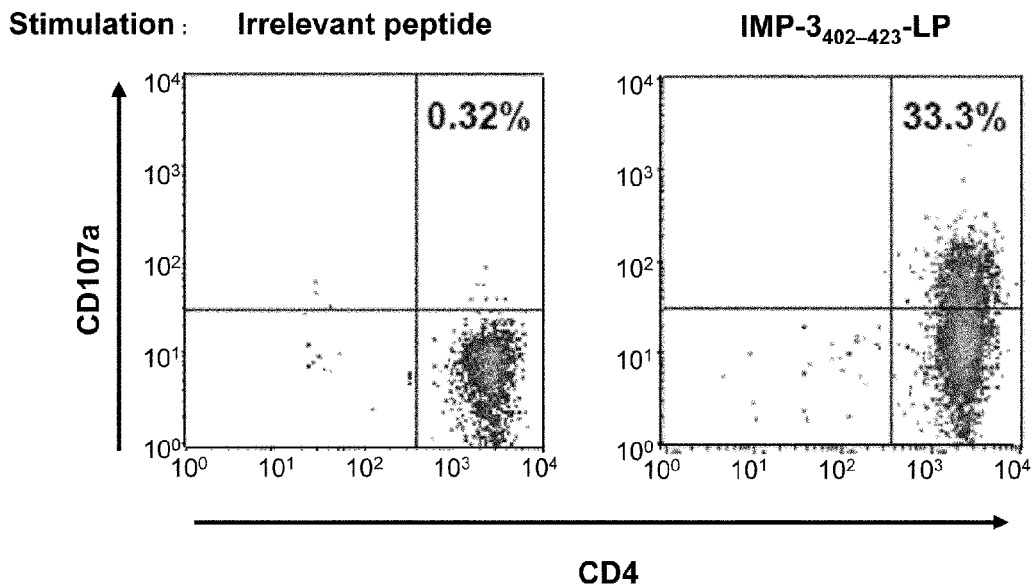

[Fig. 5]
A
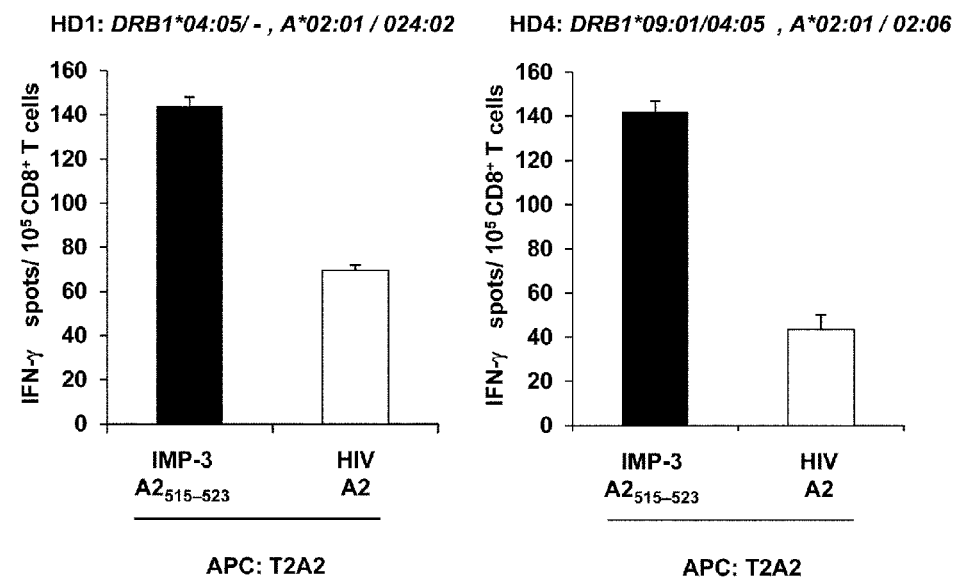
B
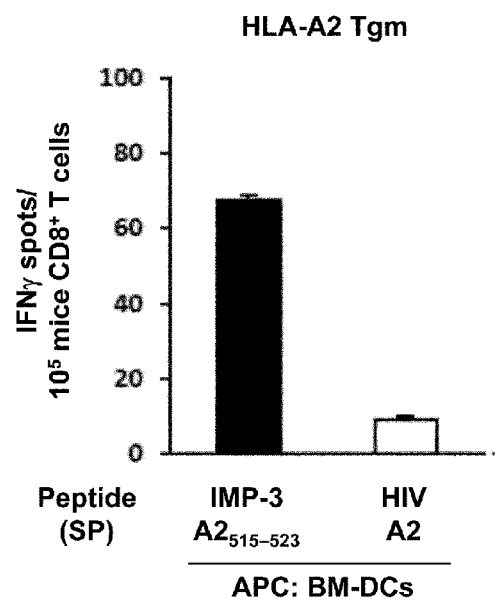

SEQUENCE LISTING

```
<160> NUMBER OF SEQ ID NOS: 6

<210> SEQ ID NO 1
<211> LENGTH: 22
<212> TYPE: PRT
<213> ORGANISM: Artificial Sequence
<220> FEATURE:
<223> OTHER INFORMATION: Th1 epitope peptide

<400> SEQUENCE: 1

Gln Ser Glu Thr Glu Thr Val His Leu Phe Ile Pro Ala Leu Ser Val
1               5                   10                  15

Gly Ala Ile Ile Gly Lys
            20

<210> SEQ ID NO 2
<211> LENGTH: 21
<212> TYPE: PRT
<213> ORGANISM: Artificial Sequence
<220> FEATURE:
<223> OTHER INFORMATION: Th1 epitope peptide

<400> SEQUENCE: 2

Gly Lys Thr Val Asn Glu Leu Gln Asn Leu Ser Ser Ala Glu Val Val
1               5                   10                  15

Val Pro Arg Asp Gln
            20

<210> SEQ ID NO 3
<211> LENGTH: 9
<212> TYPE: PRT
<213> ORGANISM: Artificial Sequence
<220> FEATURE:
<223> OTHER INFORMATION: CTL epitope peptide

<400> SEQUENCE: 3

Lys Thr Val Asn Glu Leu Gln Asn Leu
1               5

<210> SEQ ID NO 4
<211> LENGTH: 9
<212> TYPE: PRT
<213> ORGANISM: Artificial Sequence
<220> FEATURE:
<223> OTHER INFORMATION: CTL epitope peptide

<400> SEQUENCE: 4

Asn Leu Ser Ser Ala Glu Val Val Val
1               5

<210> SEQ ID NO 5
<211> LENGTH: 4168
<212> TYPE: DNA
<213> ORGANISM: Homo sapiens
```

```
<220> FEATURE:
<221> NAME/KEY: CDS
<222> LOCATION: (267)..(2006)

<400> SEQUENCE: 5
aagacttagg aagactggtg gatgcgtttg ggttgtagct aggcttttc ttttctttct      60 cttttaaaac acatctagac aaggaaaaaa caagcctcgg atctgatttt tcactcctcg    120
ttcttgtgct tggttcttac tgtgtttgtg tattttaaag gcgagaagac gaggggaaca    180
aaaccagctg gatccatcca tcaccgtggg tggttttaat ttttcgtttt ttctcgttat    240
ttttttttaa acaaccactc ttcaca atg aac aaa ctg tat atc gga aac ctc    293
                              Met Asn Lys Leu Tyr Ile Gly Asn Leu
                               1               5 agc gag aac gcc gcc ccc tcg gac cta gaa agt atc ttc aag gac gcc    341
Ser Glu Asn Ala Ala Pro Ser Asp Leu Glu Ser Ile Phe Lys Asp Ala
 10              15                  20                  25 aag atc ccg gtg tcg gga ccc ttc ctg gtg aag act ggc tac gcg ttc    389
Lys Ile Pro Val Ser Gly Pro Phe Leu Val Lys Thr Gly Tyr Ala Phe
             30                  35                  40 gtg gac tgc ccg gac gag agc tgg gcc ctc aag gcc atc gag gcg ctt    437
Val Asp Cys Pro Asp Glu Ser Trp Ala Leu Lys Ala Ile Glu Ala Leu
         45                  50                  55 tca ggt aaa ata gaa ctg cac ggg aaa ccc ata gaa gtt gag cac tcg    485
Ser Gly Lys Ile Glu Leu His Gly Lys Pro Ile Glu Val Glu His Ser
     60                  65                  70 gtc cca aaa agg caa agg att cgg aaa ctt cag ata cga aat atc ccg    533
Val Pro Lys Arg Gln Arg Ile Arg Lys Leu Gln Ile Arg Asn Ile Pro
 75                  80                  85 cct cat tta cag tgg gag gtg ctg gat agt tta cta gtc cag tat gga    581
Pro His Leu Gln Trp Glu Val Leu Asp Ser Leu Leu Val Gln Tyr Gly
 90                  95                 100                 105 gtg gtg gag agc tgt gag caa gtg aac act gac tcg gaa act gca gtt    629
Val Val Glu Ser Cys Glu Gln Val Asn Thr Asp Ser Glu Thr Ala Val
                110                 115                 120 gta aat gta acc tat tcc agt aag gac caa gct aga caa gca cta gac    677
Val Asn Val Thr Tyr Ser Ser Lys Asp Gln Ala Arg Gln Ala Leu Asp
            125                 130                 135 aaa ctg aat gga ttt cag tta gag aat ttc acc ttg aaa gta gcc tat    725
Lys Leu Asn Gly Phe Gln Leu Glu Asn Phe Thr Leu Lys Val Ala Tyr
        140                 145                 150 atc cct gat gaa atg gcc gcc cag caa aac ccc ttg cag cag ccc cga    773
Ile Pro Asp Glu Met Ala Ala Gln Gln Asn Pro Leu Gln Gln Pro Arg
    155                 160                 165 ggt cgc cgg ggg ctt ggg cag agg ggc tcc tca agg cag ggg tct cca    821
Gly Arg Arg Gly Leu Gly Gln Arg Gly Ser Ser Arg Gln Gly Ser Pro
170                 175                 180                 185 gga tcc gta tcc aag cag aaa cca tgt gat ttg cct ctg cgc ctg ctg    869
Gly Ser Val Ser Lys Gln Lys Pro Cys Asp Leu Pro Leu Arg Leu Leu
                190                 195                 200 gtt ccc acc caa ttt gtt gga gcc atc ata gga aaa gaa ggt gcc acc    917
Val Pro Thr Gln Phe Val Gly Ala Ile Ile Gly Lys Glu Gly Ala Thr
            205                 210                 215 att cgg aac atc acc aaa cag acc cag tct aaa atc gat gtc cac cgt    965
Ile Arg Asn Ile Thr Lys Gln Thr Gln Ser Lys Ile Asp Val His Arg
        220                 225                 230 aaa gaa aat gcg ggg gct gct gag aag tcg att act atc ctc tct act   1013
Lys Glu Asn Ala Gly Ala Ala Glu Lys Ser Ile Thr Ile Leu Ser Thr
    235                 240                 245 cct gaa ggc acc tct gcg gct tgt aag tct att ctg gag att atg cat   1061
Pro Glu Gly Thr Ser Ala Ala Cys Lys Ser Ile Leu Glu Ile Met His
```

| | | | | | | | | | | | | | | | |
|---|---|---|---|---|---|---|---|---|---|---|---|---|---|---|---|
| Pro | Glu | Gly | Thr | Ser | Ala | Ala | Cys | Lys | Ser | Ile | Leu | Glu | Ile | Met | His |
| 250 | | | | 255 | | | | | 260 | | | | | 265 | |

```
aag gaa gct caa gat ata aaa ttc aca gaa gag atc ccc ttg aag att      1109
Lys Glu Ala Gln Asp Ile Lys Phe Thr Glu Glu Ile Pro Leu Lys Ile
                    270                 275                 280 tta gct cat aat aac ttt gtt gga cgt ctt att ggt aaa gaa gga aga      1157
Leu Ala His Asn Asn Phe Val Gly Arg Leu Ile Gly Lys Glu Gly Arg
                285                 290                 295 aat ctt aaa aaa att gag caa gac aca gac act aaa atc acg ata tct      1205
Asn Leu Lys Lys Ile Glu Gln Asp Thr Asp Thr Lys Ile Thr Ile Ser
            300                 305                 310 cca ttg cag gaa ttg acg ctg tat aat cca gaa cgc act att aca gtt      1253
Pro Leu Gln Glu Leu Thr Leu Tyr Asn Pro Glu Arg Thr Ile Thr Val
        315                 320                 325 aaa ggc aat gtt gag aca tgt gcc aaa gct gag gag gag atc atg aag      1301
Lys Gly Asn Val Glu Thr Cys Ala Lys Ala Glu Glu Glu Ile Met Lys
330                 335                 340                 345 aaa atc agg gag tct tat gaa aat gat att gct tct atg aat ctt caa      1349
Lys Ile Arg Glu Ser Tyr Glu Asn Asp Ile Ala Ser Met Asn Leu Gln
                350                 355                 360 gca cat tta att cct gga tta aat ctg aac gcc ttg ggt ctg ttc cca      1397
Ala His Leu Ile Pro Gly Leu Asn Leu Asn Ala Leu Gly Leu Phe Pro
                365                 370                 375 ccc act tca ggg atg cca cct ccc acc tca ggg ccc cct tca gcc atg      1445
Pro Thr Ser Gly Met Pro Pro Pro Thr Ser Gly Pro Pro Ser Ala Met
            380                 385                 390 act cct ccc tac ccg cag ttt gag caa tca gaa acg gag act gtt cat      1493
Thr Pro Pro Tyr Pro Gln Phe Glu Gln Ser Glu Thr Glu Thr Val His
        395                 400                 405 ctg ttt atc cca gct cta tca gtc ggt gcc atc atc ggc aag cag ggc      1541
Leu Phe Ile Pro Ala Leu Ser Val Gly Ala Ile Ile Gly Lys Gln Gly
410                 415                 420                 425 cag cac atc aag cag ctt tct cgc ttt gct gga gct tca att aag att      1589
Gln His Ile Lys Gln Leu Ser Arg Phe Ala Gly Ala Ser Ile Lys Ile
                430                 435                 440 gct cca gcg gaa gca cca gat gct aaa gtg agg atg gtg att atc act      1637
Ala Pro Ala Glu Ala Pro Asp Ala Lys Val Arg Met Val Ile Ile Thr
                445                 450                 455 gga cca cca gag gct cag ttc aag gct cag gga aga att tat gga aaa      1685
Gly Pro Pro Glu Ala Gln Phe Lys Ala Gln Gly Arg Ile Tyr Gly Lys
            460                 465                 470 att aaa gaa gaa aac ttt gtt agt cct aaa gaa gag gtg aaa ctt gaa      1733
Ile Lys Glu Glu Asn Phe Val Ser Pro Lys Glu Glu Val Lys Leu Glu
475                 480                 485 gct cat atc aga gtg cca tcc ttt gct gct ggc aga gtt att gga aaa      1781
Ala His Ile Arg Val Pro Ser Phe Ala Ala Gly Arg Val Ile Gly Lys
                490                 495                 500                 505 gga ggc aaa acg gtg aat gaa ctt cag aat ttg tca agt gca gaa gtt      1829
Gly Gly Lys Thr Val Asn Glu Leu Gln Asn Leu Ser Ser Ala Glu Val
                510                 515                 520 gtt gtc cct cgt gac cag aca cct gat gag aat gac caa gtg gtt gtc      1877
Val Val Pro Arg Asp Gln Thr Pro Asp Glu Asn Asp Gln Val Val Val
            525                 530                 535 aaa ata act ggt cac ttc tat gct tgc cag gtt gcc cag aga aaa att      1925
Lys Ile Thr Gly His Phe Tyr Ala Cys Gln Val Ala Gln Arg Lys Ile
        540                 545                 550 cag gaa att ctg act cag gta aag cag cac caa caa cag aag gct ctg      1973
Gln Glu Ile Leu Thr Gln Val Lys Gln His Gln Gln Gln Lys Ala Leu
555                 560                 565
```

```
caa agt gga cca cct cag tca aga cgg aag taa aggctcagga aacagcccac      2026
Gln Ser Gly Pro Pro Gln Ser Arg Arg Lys
570                 575 cacagaggca gatgccaaac caaagacaga ttgcttaacc aacagatggg cgctgacccc      2086
ctatccagaa tcacatgcac aagttttac ctagccagtt gtttctgagg accaggcaac       2146
```
(ctatccagaa tcacatgcac aagtttttac ctagccagtt gtttctgagg accaggcaac     2146)
```
ttttgaactc ctgtctctgt gagaatgtat actttatgct ctctgaaatg tatgacaccc      2206
agctttaaaa caaacaaaca aacaaacaaa aaaagggtgg gggagggagg gaaagagaag      2266
agctctgcac ttcccttgt tgtagtctca cagtataaca gatattctaa ttcttcttaa       2326
```
(agctctgcac ttccctttgt tgtagtctca cagtataaca gatattctaa ttcttcttaa    2326)
```
tattccccca taatgccaga aattggctta atgatgcttt cactaaattc atcaaataga      2386
ttgctcctaa atccaattgt taaaattgga tcagaataat tatcacagga acttaaatgt      2446
taagccatta gcatagaaaa actgttctca gttttatttt tacctaacac taacatgagt      2506
aacctaaggg aagtgctgaa tggtgttggc aggggtatta aacgtgcatt tttactcaac      2566
tacctcaggt attcagtaat acaatgaaaa gcaaaattgt tcctttttt tgaaaatttt       2626 atatactta taatgataga agtccaaccg ttttttaaaa ataaattta aaatttaaca        2686 gcaatcagct aacaggcaaa ttaagatttt tacttctggc tggtgacagt aaagctggaa      2746
aattaatttc agggttttt gaggcttttg acacagttat tagttaaatc aaatgttcaa       2806
aaatacggag cagtgcctag tatctggaga gcagcactac catttattct tcatttata       2866 gttgggaaag ttttgacgg tactaacaaa gtggtcgcag gagattttgg aacggctggt       2926
ttaaatggct tcaggagact tcagtttttt gtttagctac atgattgaat gcataataaa      2986
tgctttgtgc ttctgactat caatacctaa agaaagtgca tcagtgaaga gatgcaagac     3046
tttcaactga ctggcaaaaa gcaagcttta gcttgtctta taggatgctt agtttgccac     3106
tacacttcag accaatggga cagtcataga tggtgtgaca gtgtttaaac gcaacaaaag     3166
gctacatttc catggggcca gcactgtcat gagcctcact aagctatttt gaagattttt     3226
aagcactgat aaattaaaaa aaaaaaatta gactccacct taagtagtaa agtataacag     3286
gatttctgta tactgtgcaa tcagttcttt gaaaaaaaag tcaaagata gagaatacaa      3346 gaaaagtttt tgggatataa tttgaatgac tgtgaaaaca tatgaccttt gataacgaac     3406
tcatttgctc actccttgac agcaaagccc agtacgtaca attgtgttgg gtgtgggtgg     3466
tctccaaggc cacgctgctc tctgaattga tttttgagt tttgtttgta agatgatcac      3526
agtcatgtta cactgatcta aaggacatat atataaccct ttaaaaaaaa aatcactgcc     3586 tcattccttat ttcaagatga atttctatac agactagatg tttttctgaa gatcaattag    3646
```
(tcattcttat ttcaagatga atttctatac agactagatg tttttctgaa gatcaattag   3646)
```
acatttgaa aatgatttaa agtgttttcc ttaatgttct ctgaaaacaa gtttcttttg      3706
tagttttaac caaaaaagtg ccctttttgt cactggattc tcctagcatt catgatttt      3766 ttttcataca atgaattaaa attgctaaaa tcatggactg gctttctggt tggatttcag    3826
gtaagatgtg tttaaggcca gagctttct cagtatttga ttttttccc caatatttga      3886 tttttaaaa atatacacat aggtgctgca tttatatctg ctggtttaaa ttctgtcata    3946
tttcacttct agccttttag tatggcaaat catattttac ttttacttaa gcatttgtaa   4006
tttggagtat ctggtactag ctaagaaata attctataat tgagttttgt actcaccata   4066
tatggatcat tcctcatgta taatgtgccc caaatgcagc ttcattttcc agataccttg   4126
acgcagaata aatttttca tcatttaggt gcaaaaaaaa aa                        4168
```

<210> SEQ ID NO 6
<211> LENGTH: 579

<212> TYPE: PRT
<213> ORGANISM: Homo sapiens

<400> SEQUENCE: 6

Met Asn Lys Leu Tyr Ile Gly Asn Leu Ser Glu Asn Ala Ala Pro Ser
1               5                   10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

Gly Lys Pro Ile Glu Val Glu His Ser Val Pro Lys Arg Gln Arg Ile
65                  70                  75                  80

Arg Lys Leu Gln Ile Arg Asn Ile Pro Pro His Leu Gln Trp Glu Val
                85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
130                 135                 140

Glu Asn Phe Thr Leu Lys Val Ala Tyr Ile Pro Asp Glu Met Ala Ala
145                 150                 155                 160

Gln Gln Asn Pro Leu Gln Gln Pro Arg Gly Arg Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
        195                 200                 205

Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
            260                 265                 270

Phe Thr Glu Glu Ile Pro Leu Lys Ile Leu Ala His Asn Asn Phe Val
        275                 280                 285

Gly Arg Leu Ile Gly Lys Glu Gly Arg Asn Leu Lys Lys Ile Glu Gln
    290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Glu Ile Met Lys Lys Ile Arg Glu Ser Tyr Glu
            340                 345                 350

Asn Asp Ile Ala Ser Met Asn Leu Gln Ala His Leu Ile Pro Gly Leu
        355                 360                 365

Asn Leu Asn Ala Leu Gly Leu Phe Pro Pro Thr Ser Gly Met Pro Pro
    370                 375                 380

Pro Thr Ser Gly Pro Pro Ser Ala Met Thr Pro Pro Tyr Pro Gln Phe
385                 390                 395                 400

```
Glu Gln Ser Glu Thr Glu Thr Val His Leu Phe Ile Pro Ala Leu Ser
                405             410                 415

Val Gly Ala Ile Ile Gly Lys Gln Gly Gln His Ile Lys Gln Leu Ser
            420             425                 430

Arg Phe Ala Gly Ala Ser Ile Lys Ile Ala Pro Ala Glu Ala Pro Asp
        435             440             445

Ala Lys Val Arg Met Val Ile Ile Thr Gly Pro Pro Glu Ala Gln Phe
    450             455             460

Lys Ala Gln Gly Arg Ile Tyr Gly Lys Ile Lys Glu Glu Asn Phe Val
465             470             475                         480

Ser Pro Lys Glu Glu Val Lys Leu Glu Ala His Ile Arg Val Pro Ser
            485             490                 495

Phe Ala Ala Gly Arg Val Ile Gly Lys Gly Gly Lys Thr Val Asn Glu
            500             505             510

Leu Gln Asn Leu Ser Ser Ala Glu Val Val Val Pro Arg Asp Gln Thr
        515             520             525

Pro Asp Glu Asn Asp Gln Val Val Val Lys Ile Thr Gly His Phe Tyr
        530             535             540

Ala Cys Gln Val Ala Gln Arg Lys Ile Gln Glu Ile Leu Thr Gln Val
545             550             555                         560

Lys Gln His Gln Gln Gln Lys Ala Leu Gln Ser Gly Pro Pro Gln Ser
                565             570             575

Arg Arg Lys
```

IMP-3 EPITOPE PEPTIDES FOR TH1 CELLS AND VACCINES CONTAINING THE SAME

TECHNICAL FIELD

The present invention relates to the field of biological science, more specifically to the field of cancer therapy. In particular, the present invention relates to novel peptides that are extremely effective as cancer vaccines, and drugs for either or both of treating and preventing tumors.

CROSS-REFERENCES TO RELATED APPLICATIONS

The present application is a National Stage of International Application No. PCT/JP2014/002678, filed May 22, 2014, and which claims the benefit of Japanese Patent Application No. JP 2013-109567, filed on May 24, 2013, the entire contents of which are incorporated by reference herein.

REFERENCE TO SEQUENCE LISTING

This application includes a Sequence Listing as a text file named "087331-0963973-SEQLIST.txt" created Nov. 4, 2015, and containing 18,090 bytes. The material contained in this text file is incorporated by reference in its entirety for all purposes.

BACKGROUND ART

CD8 positive cytotoxic T lymphocytes (CTLs) have been shown to recognize epitope peptides derived from the tumor-associated antigens (TAAs) found on the major histocompatibility complex (MHC) class I molecule, and then kill the tumor cells. Since the discovery of the melanoma antigen (MAGE) family as the first example of TAAs, many other TAAs have been discovered, primarily through immunological approaches (NPL 1, 2). Some of these TAAs are currently undergoing clinical development as immunotherapeutic targets.

TAAs which are indispensable for proliferation and survival of cancer cells are valiant as targets for immunotherapy, because the use of such TAAs may minimize the well-described risk of immune escape of cancer cells attributable to deletion, mutation, or down-regulation of TAAs as a consequence of therapeutically driven immune selection. Accordingly, the identification of new TAAs capable of inducing potent and specific anti-tumor immune responses, warrants further development. Thus the clinical application of peptide vaccination strategies for various types of cancer is ongoing (NPL 3-10). To date, there have been several reports of clinical trials using these tumor-associated antigen derived peptides. Unfortunately, so far these cancer vaccine trials have yielded only a low objective response rate has been observed in these cancer vaccine trials so far (NPL 11-13). Accordingly, there remains a need in the art for new TAAs suitable for use as immunotherapeutic targets.

Recently, the present inventors have identified an oncofetal antigen, insulin-like growth factor II mRNA-binding protein 3 (IMP-3), that is frequently overexpressed in lung cancer, head-and-neck cancer (HNC), esophageal cancer and various other malignancies using genome-wide cDNA microarray analysis (NPL 14, PTL 1-3).1 The present inventors have also identified highly immunogenic IMP-3-derived short peptides (SPs) that can induce HLA-A2 (A*02:01)-restricted CTLs and HLA-A24 (A*24:02)-restricted CTLs from peripheral blood mononuclear cells (PBMCs) of lung cancer patients (NPL 14, 15, PTL 2, 3). Therefore, IMP-3 remains an attractive target molecule for cancer immunotherapy. Phase I/II clinical trials of cancer immunotherapy for lung cancer, head and neck cancer (HNC), esophageal cancer, and colorectal cancer using IMP-3-derived CTL-epitopes are underway (NPL 14-18).

Tumor-specific $CD4^+$ helper T (Th) cells, especially T-helper type 1 (Th1) cells play a critical role in efficient induction of CTL-mediated antitumor immunity (NPL 19). The IFN-gamma primarily produced by Th1 cells is critical for induction and maintenance of long lived CTL responses, providing help through multiple interactions which are critical in the preservation of immunological memory (NPL 20, 21). The IFN-gamma secreted by Th1 cells also mediates direct antitumor or anti-angiogenic effect (NPL 22). Furthermore, it has been shown that Th cells must pave the way for entry of CTLs at tumor site (NPL 23). Therefore, identification of tumor-associated antigen (TAA)-derived Th cell epitopes that can activate specific Th1 cell is important for induction of an effective tumor immunity in tumor-bearing hosts; ideally, the design of effective vaccines should include multiple epitopes to stimulate both CTL and Th1 cells (NPL 24). However, no such epitope derived from IMP-3 has yet been identified.

CITATION LIST

Patent Literature

[PTL 1] WO2004/031413
[PTL 2] WO2007/013665
[PTL 3] WO2007/013671
[PTL 4] WO2006/090810
[PTL 5] WO2011/067920

Non Patent Literature

[NPL 1] Boon T, Int J Cancer 1993 May 8, 54(2): 177-80
[NPL 2] Boon T and van der Bruggen P, J Exp Med 1996 Mar. 1, 183(3): 725-9
[NPL 3] Harris C C, J Natl Cancer Inst 1996 Oct. 16, 88(20): 1442-55
[NPL 4] Butterfield L H et al., Cancer Res 1999 Jul. 1, 59(13): 3134-42
[NPL 5] Vissers J L et al., Cancer Res 1999 Nov. 1, 59(21): 5554-9
[NPL 6] van der Burg S H et al., J Immunol 1996 May 1, 156(9): 3308-14
[NPL 7] Tanaka F et al., Cancer Res 1997 Oct. 15, 57(20): 4465-8
[NPL 8] Fujie T et al., Int J Cancer 1999 Jan. 18, 80(2): 169-72
[NPL 9] Kikuchi M et al., Int J Cancer 1999 May 5, 81(3): 459-66
[NPL 10] Oiso M et al., Int J Cancer 1999 May 5, 81(3): 387-94
[NPL 11] Belli F et al., J Clin Oncol 2002 Oct. 15, 20(20): 4169-80
[NPL 12] Coulie P G et al., Immunol Rev 2002 October, 188: 33-42
[NPL 13] Rosenberg S A et al., Nat Med 2004 September, 10(9): 909-15
[NPL 14] Tomita Y, et al., Cancer Sci 2011; 102:71-8.
[NPL 15] Suda T, et al., Cancer Sci 2007; 98:1803-8.
[NPL 16] Mizukami Y, et al., Cancer Sci 2008; 99:1448-54.
[NPL 17] Kono K, et al., Cancer Sci 2009; 100:1502-9.

[NPL 18] Kono K, et al., J Transl Med 2012; 10:141.
[NPL 19] Chamoto K et al. Cancer Res 2004; 64: 386-90.
[NPL 20] Bevan M J. Nat Rev Immunol 2004; 4: 595-602.
[NPL 21] Shedlock D J and Shen H. Science 2003; 300: 337-9.
[NPL 22] Street S E et al. Blood 2001; 97: 192-7.
[NPL 23] Bos R, and Sherman L A. Cancer Res; 70: 8368-77.
[NPL 24] Melief C J et al. Nat Rev Cancer 2008; 8: 351-60.

SUMMARY OF INVENTION

In the context of the present invention, the present inventors considered an ideal peptide vaccine for cancer immunotherapy to be one that includes a single polypeptide containing epitopes for both CTL and Th1 cell, both of which are naturally proximal to each other (Kenter G G et al. N Engl J Med 2009; 361: 1838-47).

To that end, the present inventors designed a strategy to identify novel IMP-3-derived Th1 cell epitopes recognized in the context of promiscuous HLA class II molecules and containing CTL epitopes, working on the presumption that epitopes so characterized would induce more efficient T cell-mediated tumor immunity. A computer algorithm predicting HLA class II-binding peptides and known CTL epitope sequences recognized by HLA-A24 (A*24:02) or HLA-A2 (A*0201)-restricted CTLs was used to select candidate promiscuous HLA-class II-restricted Th1 cell epitopes containing CTL epitopes.

The present invention is based, at least in part, on the discovery of suitable epitope peptides that serve as targets of immunotherapy for inducing Th1 cell response. Recognizing that the IMP-3 gene is up-regulated in a number of cancer types, including bladder cancer, cervical cancer, cholangiocellular carcinoma, chronic myelocytic leukemia, colon cancer, rectum cancer, esophageal cancer, gastric diffuse-type cancer, non-small-cell lung cancer (NSCLC), small-cell lung cancer (SCLC), lymphoma, osteosarcoma, ovarian cancer, renal carcinoma, soft tissue tumor, testicular tumor, and HNC, the present invention targets for further analysis the gene product of IMP-3 gene, more particularly the polypeptide exemplary set forth in SEQ ID NO: 6, which is encoded by the gene of GenBank Accession No. NM_006547.2 (SEQ ID NO: 5). IMP-3 gene products containing epitope peptides that elicit Th1 cells specific to the corresponding molecule were particularly selected for further study. For example, peripheral blood mononuclear cells (PBMCs) obtained from a healthy donor were stimulated using promiscuous HLA-DRs and/or DPs binding peptide derived from human IMP-3. Th1 cells that recognize HLA-DRs or DPs positive target cells pulsed with the respective candidate peptides were established, and HLA-DRs and/or DPs restricted epitope peptides that can induce potent and specific immune responses against IMP-3 were identified. These results demonstrate that IMP-3 is strongly immunogenic and the epitopes thereof are effective for tumor immunotherapy mediated through Th1 cell response. Additional studies revealed that the promiscuous HLA-DRs and/or DPs binding peptides containing at least one CTL epitope can also stimulate CTL response in the same donor in a IMP-3 specific manner. These results confirm that IMP-3 is strongly immunogenic and that epitopes thereof containing both Th1 cell and CTL epitopes are effective for tumor immunotherapy mediated through both Th1 cell and CTL responses.

It is therefore an object of the present invention to provide peptides having Th1 cell inducibility as well as an amino acid sequence selected from among SEQ ID NOs: 1 and 2. The present invention contemplates modified peptides, i.e., peptides having Th1 cell inducibility that are up to 30 amino acids in length and have a contiguous amino acid sequence selected from the amino acid sequence of SEQ ID NO: 6 (IMP-3), as well as functional equivalents thereof. Alternatively, the present invention also provides peptides having both Th1 cell and CTL inducibilities. In some embodiments, the peptides of the present invention correspond to the amino acid sequence of SEQ ID NO: 1 or 2 or modified versions thereof, in which one, two or several amino acids are substituted, deleted, inserted and/or added, while the ability to induce Th1 cells is maintained.

When administered to a subject, the present peptides are preferably presented on the surface of one or more antigen-presenting cells that in turn induce Th1 cells. When the peptide of the present invention further contains at least one CTL epitope, such APCs also process the peptides to present CTL epitopes generated from the present peptides, and thus induce CTLs targeting the respective peptides. Therefore, it is a further object of the present invention to provide antigen-presenting cells presenting any of the present peptides or fragments thereof, as well as methods for inducing antigen-presenting cells.

Administration of one or more peptides of the present invention or polynucleotide(s) encoding such peptides, or antigen-presenting cells which present such peptides or fragments thereof results in the induction of a strong anti-tumor immune response. Accordingly, it is yet another object of the present invention to provide pharmaceutical agents or compositions that contain as active ingredient(s) one or more of the following: (a) one or more peptides of the present invention, (b) one or more polynucleotides encoding such peptide(s), and (c) one or more antigen-presenting cells of the present invention. Such pharmaceutical agents or compositions of the present invention find particular utility as vaccines.

It is yet a further object of the present invention to provide methods for the treatment and/or prophylaxis (i.e., prevention) of cancers (i.e., tumors), and/or prevention of postoperative recurrence thereof. Methods for inducing Th1 cells or for inducing anti-tumor immunity that include the step of administering one or more peptides, polynucleotides, antigen-presenting cells or pharmaceutical agents or compositions of the present invention are also contemplated. Furthermore, the Th1 cells of the present invention also find use as vaccines against cancer, examples of which include, but are not limited to, bladder cancer, cervical cancer, cholangiocellular carcinoma, chronic myelocytic leukemia, colon cancer, rectum cancer, esophageal cancer, gastric diffuse-type cancer, non-small-cell lung cancer (NSCLC), small-cell lung cancer (SCLC), lymphoma, osteosarcoma, ovarian cancer, renal carcinoma, soft tissue tumor, testicular tumor, and HNC.

Examples of specifically contemplated objects of the present invention include the following:

[1] An isolated peptide having 10-30 amino acids in length and comprising a part of the amino acid sequence of SEQ ID NO: 6, wherein said peptide comprises an amino acid sequence selected from the group consisting of:

(a) a contiguous amino acid sequence having more than 9 amino acids in length selected from the amino acid sequence of SEQ ID NO: 1 or 2; and (b) an amino acid sequence in which one, two or several amino acids are substituted, deleted, inserted, and/or added in the amino acid sequence of (a), wherein said peptide has ability to induce T helper type 1 (Th1) cells.

[2] The isolated peptide of [1], wherein the peptide or fragment thereof has abilities to bind at least two kinds of MHC class II molecules.

[3] The isolated peptide of [2], wherein the MHC class II molecules are selected from the group consisting of HLA-DR8, HLA-DR53, HLA-DR14, and HLA-DR9.

[4] The isolated peptide of any one of [1] to [3], wherein said peptide comprises an amino acid sequence of a peptide having IMP-3-specific cytotoxic T lymphocyte (CTL) inducibility.

[5] The isolated peptide of [4], wherein said peptide comprises the amino acid sequence selected from the group consisting of:
 (a) an amino acid sequence selected from the group consisting of SEQ ID NOs: 1 and 2; and
 (b) an amino acid sequence in which one, two or several amino acids are substituted, deleted, inserted, and/or added in the amino acid sequence of (a).

[6] An isolated polynucleotide encoding the peptide of any one of [1] to [5].

[7] A composition for inducing at least one of the cells selected from the group consisting of
 (i) Th1 cells,
 (ii) CTLs,
 (iii) antigen-presenting cells (APCs) having an ability to induce Th1 cells, and
 (iv) APCs having an ability to induce CTLs,
 wherein the composition comprises one or more peptide(s) of any one of [1] to [5], or one or more polynucleotide(s) encoding them, or a composition for inducing at least one type of cell selected from the group consisting of
 (i) Th1 cells,
 (ii) CTLs,
 (iii) antigen-presenting cells (APCs) having an ability to induce Th1 cells, and
 (iv) APCs having an ability to induce CTLs,
 wherein the composition comprises one or more peptide(s) of any one of [1] to [5], or one or more polynucleotide(s) encoding them.

[8] A pharmaceutical composition, wherein the composition comprises at least one active ingredient selected from the group consisting of:
 (a) one or more peptide(s) of any one of [1] to [5];
 (b) one or more polynucleotide(s) of [6];
 (c) one or more APC(s) presenting the peptide of any one of [1] to [5] or fragment thereof on their surface;
 (d) one or more Th1 cells that recognize(s) an APC presenting the peptide of any one of [1] to [5] or fragment thereof on its surface; and
 (e) combination of any two or more of (a) to (d) above; and is formulated for a purpose selected from the group consisting of:
 (i) cancer treatment,
 (ii) cancer prevention,
 (iii) prevention of post-operative recurrence in cancer, and
 (iv) combinations of any two or more of (i) to (iii) above.

[9] The pharmaceutical composition of [8], wherein said composition is formulated for administration to a subject that has at least one selected from the group consisting of HLA-DR8, HLA-DR53, HLA-DR14, and HLA-DR9 as an MHC class II molecule, or the pharmaceutical composition of [8], wherein said composition is formulated for administration to a subject that has at least one MHC class II molecule selected from the group consisting of HLA-DR8, HLA-DR53, HLA-DR14, and HLA-DR9.

[10] The pharmaceutical composition of [8] or [9], wherein said composition further comprises one or more peptides having CTL inducibility.

[11] A composition for enhancing an immune response mediated with an MHC class II molecule, wherein the composition comprises at least one active ingredient selected from the group consisting of:
 (a) one or more peptide(s) of any one of [1] to [5];
 (b) one or more polynucleotide(s) of [6];
 (c) one or more APC(s) presenting the peptide of any one of [1] to [5] or fragment thereof on their surface;
 (d) one or more Th1 cell(s) that recognize(s) an APC presenting the peptide of any one of [1] to [5] or fragment thereof on its surface; and
 (e) combination of any two or more of (a) to (d) above.

[12] A method for inducing an APC having an ability to induce a Th1 cell, said method comprising a step of contacting an APC with the peptide of any one of [1] to [5] in vitro, ex vivo or in vivo.

[13] A method for inducing an APC having an ability to induce a CTL, said method comprising a step selected from the group consisting of:
 (a) contacting an APC with the peptide of any one of [1] to [5] in vitro, ex vivo or in vivo; and
 (b) introducing a polynucleotide encoding the peptide of any one of [1] to [5] into an APC.

[14] A method for inducing a Th1 cell, said method comprising a step selected from the group consisting of:
 (a) co-culturing a CD4-positive T cell with an APC that presents on its surface a complex of an MHC class II molecule and the peptide of any one of [1] to [5] or fragment thereof; and
 (b) introducing a polynucleotide encoding both of T cell receptor (TCR) subunits, or polynucleotides encoding each of TCR subunits into a CD4-positive T cell, wherein the TCR can bind to a complex of an MHC class II molecule and the peptide of any one of [1] to [5] or fragment thereof presented on cell surface, or a method for inducing a Th1 cell, said method comprising a step selected from the group consisting of:
 (a) co-culturing a CD4-positive T cell with an APC that presents on its surface a complex of an MHC class II molecule and the peptide of any one of [1] to [5] or fragment thereof; and
 (b) introducing a single polynucleotide encoding both of T cell receptor (TCR) subunits, or multiple polynucleotides each encoding a separate TCR subunit into a CD4-positive T cell, wherein the TCR can bind to a complex of an MHC class II molecule and the peptide of any one of [1] to [5] or fragment thereof presented on a cell surface if an APC.

[15] A method for inducing a CTL, said method comprising the step selected from the group consisting of:
 (a) co-culturing both of a CD4-positive T cell and a CD8-positive T cell with APCs contacted with the peptide of [4] or [5]; and
 (b) co-culturing a CD8-positive T cell with an APC contacted with the peptide of [4] or [5].

[16] A method for enhancing an immune response mediated by an MHC class II molecule, wherein the method comprises a step of administering to a subject at least one active ingredient selected from the group consisting of:
 (a) one or more peptide(s) of any one of [1] to [5];
 (b) one or more polynucleotide(s) of [6];
 (c) one or more APC(s) presenting the peptide of any one of [1] to [5] or fragment thereof on their surface;

(d) one or more Th1 cell(s) that recognize(s) an APC presenting the peptide of any one of [1] to [5] or fragment thereof on its surface; and (e) combination of any two or more of (a) to (d) above.

[17] An isolated APC that presents on its surface a complex of an MHC class II molecule and the peptide of any one of [1] to [5] or fragment thereof.

[18] The APC induced by the method of [12] or [13].

[19] An isolated Th1 cell that recognizes the peptide of any one of [1] to [5] or fragment thereof presented on a surface of an APC.

[20] The Th1 cell induced by the method of [14].

[21] A method of inducing an immune response against cancer in a subject in need thereof, said method comprising the step of administering to the subject a composition comprising at least one active ingredient selected from the group consisting of:

(a) one or more peptide(s) of any one of [1] to [5];

(b) one or more polynucleotide(s) of [6];

(c) one or more APC(s) presenting the peptide of any one of [1] to [5] or fragment thereof on their surface;

(d) one or more Th1 cell(s) that recognize(s) an APC presenting the peptide of any one of [1] to [5] or fragment thereof on its surface; and (e) combination of any two or more of (a) to (d) above.

[22] An antibody or immunologically active fragment thereof against the peptide of any one of [1] to [5].

[23] A vector comprising a nucleotide sequence encoding the peptide of any one of [1] to [5].

[24] A host cell transformed or transfected with the expression vector of [23].

[25] A diagnostic kit comprising the peptide of any one of [1] to [5], the polynucleotide of [6] or the antibody of [22].

In addition to the above, other objects and features of the invention will become more fully apparent when the following detailed description is read in conjunction with the accompanying figures and examples. However, it is to be understood that both the foregoing summary of the invention and the following detailed description are of exemplified embodiments, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments which follows.

FIG. 1 presents IMP-3-derived and promiscuous HLA class II-binding peptides including CTL epitopes predicted by a recently developed computer algorithm. In Part A, the amino acid sequence of the human IMP-3 protein was analyzed using an algorithm (IEDB analysis resource, consensus method: tools.immuneepitope.org/analyze/html/mhc_II_binding.html). Numbers on the horizontal axis indicate amino acid positions at the N-terminus of IMP-3-derived 15-mer peptides. Higher consensus percentile rank indicates stronger binding affinity to HLA class II molecules. In Part B, the overlapping 22-mer and 21-mer LPs, IMP-$3_{402\text{-}423}$-LP and IMP-$3_{507\text{-}527}$-LP with high consensus percentile ranks for multiple HLA-class II allelic (DRB1*09:01, DRB1*04:05, and DRB1*15:02) products and 9-mer peptides recognized by HLA-A24 (IMP-3-A24$_{508\text{-}516}$) or -A2 (IMP-3-A2$_{515\text{-}523}$)-restricted CTLs were synthesized (A, black bars).

FIG. 2 presents the induction of IMP-3-specific Th cells from healthy donors. In Part A, IMP-3-specific Th cells were generated from a DR53$^+$ healthy donor (HD1) by stimulation with IMP-$3_{402\text{-}423}$-LP. The generated Th cells were re-stimulated with autologous PBMCs or L-cells pulsed with IMP-$3_{402\text{-}423}$-LP. The number of IFN-gamma-producing Th cells was analyzed by ELISPOT assay. Representative data from at least 3 independent experiments with similar results obtained from HD1 are shown. The HLA class-II genotype of donor HD1 is indicated in a top of the panels. The underlined HLA-class II alleles encode HLA-class II-molecule presenting the peptides to Th cells. In Part B, IMP-3-specific Th cells were generated from a DR53-negative, DR8-positive healthy donor (HD2) by stimulation with IMP-$3_{402\text{-}423}$-LP.

In Part C, HLA-DR-restricted IMP-$3_{402\text{-}423}$-LP-specific Th cells were generated from a healthy donor (HD3) by stimulation with IMP-$3_{402\text{-}423}$-LP. In Part D, HLA-DR-restricted IMP-$3_{507\text{-}527}$-LP-specific Th cells were generated from a healthy donor (HD3) by stimulation with IMP-$3_{507\text{-}527}$-LP. In Part E, IMP-$3_{507\text{-}527}$-LP-specific HLA-DR9-restricted Th cells were generated from a healthy donor (HD4) by stimulation with IMP-$3_{507\text{-}527}$-LP.

FIG. 3 presents the natural processing and presentation of IMP-3-LPs by DCs. In Part A, HLA-DR9-restricted IMP-$3_{507\text{-}527}$-LP-specific Th clone established from the donor-HD4 recognized autologous DCs loaded with recombinant IMP-3 protein. Representative data from 2 independent experiments with similar results are shown. In Part B, HLA-DR53-restricted and IMP-$3_{402\text{-}423}$-LP-specific Th clone established from the donor-HD1 recognized autologous DCs loaded with a recombinant IMP-3 protein.

FIG. 4 presents the cytokine profile produced by IMP-$3_{507\text{-}527}$-LP-specific bulk Th cells. In Part A, after 24 h incubation of T-cells co-cultured with autologous PBMCs in the presence of IMP-$3_{507\text{-}527}$-LP, the culture supernatant was collected and the concentration of cytokines (IFN-gamma, TNF-alpha, IL-2, GM-CSF, IL-4, and IL-17) was measured using the Bio-Plex assay system. Data are presented as the mean+/−SD of triplicate assays.

In Part B, detection of CD107a exposed on the cell surface of bulk IMP-3-specific CD4$^+$ T-cells after antigenic stimulation. Cells were restimulated with IMP-$3_{507\text{-}527}$-LP, IMP-$3_{402\text{-}423}$-LP or irrelevant peptide. Event shown are gated for CD4$^+$ T-cells. The numbers inside the plots indicate the percentage of the cell population with the quadrant characteristic (CD4$^+$ CD107a$^+$ T-cells).

FIG. 5 presents IMP-$3_{507\text{-}527}$-LP induces efficient cross-priming of CTLs in vitro and in vivo. In Part A, CD8$^+$ T cells isolated from PBMCs of healthy donors were stimulated at weekly intervals with IMP-$3_{507\text{-}527}$-LP-pulsed autologous DCs. After at least 3 rounds of stimulations, the number of IFN-gamma-producing CD8$^+$ T-cells was analyzed by INFgamma ELISPOT assay in vitro. In Part B, HLA-A2 Tgm were immunized with IMP-3$_{507-527}$-LP emulsified in IFA. After the second vaccination with IMP-3$_{507-527}$-LP, mouse CD8$^+$ T-cells in the inguinal lymph nodes were stimulated with BM-DCs pulsed with IMP-3-A2$_{515-523}$ SP or HIV-A2 SP. The number of IFN-gamma-producing mouse CD8$^+$ T-cells was analyzed by ex vivo ELISPOT. Representative data from at least 3 independent experiments with similar results are shown.

DESCRIPTION OF EMBODIMENTS

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

I. Definitions

Unless otherwise defined, all technical and scientific terms used herein have the same meaning as commonly understood by one of ordinary skill in the art to which the present invention belongs. However, in case of conflict, the present specification, including definitions, will control.

The words "a", "an", and "the" as used herein mean "at least one" unless otherwise specifically indicated.

The terms "isolated" and "purified" used in relation with a substance (e.g., peptide, antibody, polynucleotide, etc.) indicates that the substance is substantially free from at least one substance that may else be included in the natural source. Thus, an isolated or purified peptide refers to peptide that are substantially free of cellular material such as carbohydrate, lipid, or other contaminating proteins from the cell or tissue source from which the peptide is derived, or substantially free of chemical precursors or other chemicals when chemically synthesized.

The term "substantially free of cellular material" includes preparations of a peptide in which the peptide is separated from cellular components of the cells from which it is isolated or recombinantly produced. Thus, a peptide that is substantially free of cellular material includes preparations of polypeptide having less than about 30%, 20%, 10%, or 5% (by dry weight) of heterologous protein (also referred to herein as a "contaminating protein"). When the peptide is recombinantly produced, it is also preferably substantially free of culture medium, which includes preparations of peptide with culture medium less than about 20%, 10%, or 5% of the volume of the peptide preparation. When the peptide is produced by chemical synthesis, it is preferably substantially free of chemical precursors or other chemicals, which includes preparations of peptide with chemical precursors or other chemicals involved in the synthesis of the peptide less than about 30%, 20%, 10%, 5% (by dry weight) of the volume of the peptide preparation. That a particular peptide preparation contains an isolated or purified peptide can be shown, for example, by the appearance of a single band following sodium dodecyl sulfate (SDS)-polyacrylamide gel electrophoresis of the protein preparation and Coomassie Brilliant Blue staining or the like of the gel. In a preferred embodiment, peptides and polynucleotides of the present invention are isolated or purified.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogs and amino acid mimetics that similarly function to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha-carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotide" and "nucleic acid" are used interchangeably herein and, unless otherwise specifically indicated, are referred to by their commonly accepted single-letter codes.

The terms "agent" and "composition" are used interchangeably herein to refer to a product that includes specified ingredients in specified amounts, as well as any product that results, directly or indirectly, from combination of the specified ingredients in the specified amounts. Such term in relation to pharmaceutical composition, is intended to encompass a product including the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically or physiologically acceptable carrier.

The term "active ingredient" herein refers to a substance in a composition that is biologically or physiologically active. Particularly, in the context of a pharmaceutical composition, the term "active ingredient" refers to a component substance that shows an objective pharmacological effect. For example, in case of pharmaceutical compositions for use in the treatment or prevention of cancer, active ingredients in the compositions may lead to at least one biological or physiologically action on cancer cells and/or tissues directly or indirectly. Preferably, such action may include reducing or inhibiting cancer cell growth, damaging or killing cancer cells and/or tissues, and so on. Typically, indirect effect of active ingredients is inductions of immune responses mediated by MHC Class II molecules. Before being formulated, the "active ingredient" may also be referred to as "bulk", "drug substance" or "technical product". The phrase "pharmaceutically acceptable carrier" or "physiologically acceptable carrier", as used herein, means a pharmaceutically or physiologically acceptable material, composition, substance or vehicle, including, but are not limited to, a liquid or solid filler, diluent, excipient, solvent or encapsulating material.

Unless otherwise defined, the term "cancer" refers to cancers expressing IMP-3 gene, including, for example, bladder cancer, cervical cancer, cholangiocellular carcinoma, chronic myelocytic leukemia, colon cancer, rectum cancer, esophageal cancer, gastric diffuse-type cancer, non-small-cell lung cancer (NSCLC), small-cell lung cancer (SCLC), lymphoma, osteosarcoma, ovarian cancer, renal carcinoma, soft tissue tumor, testicular tumor, and HNC. Cancer expressing IMP-3 gene is also referred to as cancer expressing IMP-3, or cancer expressing the gene encoding IMP-3.

Unless otherwise defined, the terms "T lymphocyte" and "T cell" are used interchangeably herein.

Unless otherwise defined, the term "cytotoxic T lymphocyte", "cytotoxic T cell" and "CTL" are used interchangeably herein and, otherwise specifically indicated, refer to a sub-group of T lymphocytes that are capable of recognizing non-self cells (e.g., tumor cells, virus-infected cells) and inducing the death of such cells. CTLs are differentiated from CD8+ T lymphocytes and can recognize peptides presented by MHC class I molecules.

Unless otherwise defined, the term "HLA-A24" refers to the HLA-A24 type containing the subtypes, examples of which include, but are not limited to, HLA-A*2401, HLA-A*2402, HLA-A*2403, HLA-A*2404, HLA-A*2407, HLA-A*2408, HLA-A*2420, HLA-A*2425 and HLA-A*2488.

Unless otherwise defined, "HLA-A2", as used herein, representatively refers to the subtypes, examples of which include, but are not limited to, HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250.

Unless otherwise defined, the terms "T helper type 1 cell" and "Th1 cell" are used interchangeably herein and, otherwise specifically indicated, refer to a sub-group of CD4+ T lymphocytes that are capable of recognizing peptides presented by an MHC class II molecules, and associated with cellular immunity. Unless otherwise defined, the terms "Th cell", "CD4+ T cell" and "CD4+ helper T cell" are also used interchangeably herein. Th1 cells secrete a variety of cytokines (such as IFN-gamma, IL-2, TNF-beta, GM-CSF, TNF-alpha, and so on) to help activation and/or stimulation of other immune cells relating to cellular immunity (e.g, CTL, macrophage).

Unless otherwise defined, the term "HLA-DR9" refers to the subtypes, examples of which include, but are not limited to, HLA-DRB1*09:01, HLA-DRB1*09:02, HLA-DRB1*09:03, HLA-DRB1*09:04, HLA-DRB1*09:05, HLA-DRB1*09:06, HLA-DRB1*09:07, HLA-DRB1*09:08 and HLA-DRB1*09:09.

Unless otherwise defined, the term "HLA-DR14" refers to the subtypes, examples of which include, but are not limited to, HLA-DRB1*14:01, HLA-DRB1*14:02, HLA-DRB1*14:03, HLA-DRB1*14:04, HLA-DRB1*14:05, HLA-DRB1*14:06, HLA-DRB1*14:07, HLA-DRB1*14:08, and HLA-DRB1*14:10.

Unless otherwise defined, the term "HLA-DR53" refers to the subtypes, examples of which include, but are not limited to, HLA-DRB4*01:01 and HLA-DRB4*01:03.

Unless otherwise defined, the term "HLA-DR8" refers to the subtypes, examples of which include, but are not limited to, HLA-DRB1*08:01, HLA-DRB1*08:02, HLA-DRB1*08:03, LA-DRB1*08:04, HLA-DRB1*08:05, HLA-DRB1*08:06, HLA-DRB1*08:07, HLA-DRB1*08:10, HLA-DRB1*08:11 and HLA-DRB1*08:12.

Unless otherwise defined, the phrase "immune response mediated with an MHC class II molecule" refers to immune responses induced by presentation of peptide by MHC class II molecule. Herein, "immune response mediated with an MHC class II antigen" includes immune responses induced by CD4+ T cells, in particular, Th1 cells. Examples of such immune responses include, but not limited to, production of cytokines (such as IFN-gamma, IL-2, TNF-beta, GM-CSF, TNF-alpha, and so on) and activation and/or stimulation of other immune cells (such as CTL, macrophage, and so on).

Unless otherwise defined, the phrase "Th1 cell specific to IMP-3" refers to a Th1 cell that is specifically activated with an antigen presenting cell presenting a peptide derived from IMP-3, but not with other antigen presenting cells.

Unless otherwise defined, the phrase "IMP-3-specific CTL" refers to a CTL that specifically shows cytotoxicity against a target cell expressing IMP-3.

Unless otherwise defined, when used in the context of peptides, the phrase "CTL inducibility" refers to an ability of a peptide to induce a CTL when presented on an antigen-presenting cell.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g., bispecific antibodies) formed from at least two intact antibodies, and antibody fragments so long as they exhibit the desired biological activity. An "antibody" indicates all classes (e.g., IgA, IgD, IgE, IgG and IgM).

Unless otherwise defined, all technical and scientific terms used herein have the same meaning as commonly understood by one of ordinary skill in the art to which this invention belongs.

II. Peptides

Peptides of the present invention described in detail below may be referred to as "IMP-3 peptide(s)" or "IMP-3 polypeptide(s)".

To demonstrate that peptides derived from IMP-3 function as an antigen recognized by T helper type 1 (Th1) cells, peptides derived from IMP-3 (SEQ ID NO:6) were analyzed to determine whether they were antigen epitopes promiscuously restricted by MHC class II molecules. Candidates of promiscuous MHC class II binding peptides derived from IMP-3 were identified based on their binding affinities to HLA-DR8, HLA-DR53, HLA-DR14, and HLA-DR9. After in vitro stimulation of CD 4$^+$ T-cells by dendritic cells (DCs) loaded with these peptides, Th1 cells were successfully established using each of the following peptides:
IMP-3$_{402\text{-}423}$-LP/QSETETVHLFIPALSVGAIIGK (SEQ ID NO: 1), and
IMP-3$_{507\text{-}527}$-LP/GKTVNELQNLSSAEVVVPRDQ (SEQ ID NO: 2).

These established Th1 cells noted above showed potent specific Th1 cell activity in response to stimulation of antigen presenting cells pulsed with respective peptides. Furthermore, the aforementioned peptides could stimulate Th1 cells restricted by several HLA-DR and HLA-DP molecules (e.g., HLA-DR8, HLA-DR53, HLA-DR14, and HLA-DR9) which are frequently observed in the Japanese population. These results herein demonstrate that IMP-3 is an antigen recognized by Th1 cells and that the peptides are epitope peptides of IMP-3 promiscuously restricted by several HLA-class II molecules (such as HLA-DR8, HLA-DR53, HLA-DR14, and HLA-DR9).

The above identified peptides additionally contained an amino acid sequence of a CTL epitope having an ability to induce a CTL specific to IMP-3 and, as demonstrated herein, such peptides can induce CTLs specific to IMP-3 as well as Th1 cells. Accordingly, those peptides may be suitable peptides for induction of immune responses against cancer expressing IMP-3. Since the IMP-3 gene is over-expressed in most cancer tissues, including, for example, bladder cancer, cervical cancer, cholangiocellular carcinoma, chronic myelocytic leukemia, colon cancer, rectum cancer, esophageal cancer, gastric diffuse-type cancer, non-small-cell lung cancer (NSCLC), small-cell lung cancer (SCLC), lymphoma, osteosarcoma, ovarian cancer, renal carcinoma, soft tissue tumor, testicular tumor, and HNC, it represents a good target for immunotherapy.

Accordingly, the present invention provides peptides having ability induce Th1 cells specific to IMP-3. The peptides of the present invention can bind at least one MHC class II molecule and be presented on antigen presenting cells. Alternatively, the fragment of the peptides of the present invention may bind at least one MHC class II molecule and be presented on antigen presenting cells. Those fragments of the peptides may be produced by processing within antigen presenting cells. In preferred embodiments, the peptides of the present invention or fragment thereof have abilities to bind two or more kinds of MHC class II molecules (e.g., HLA-DR53 HLA-DR8, HLA-DR14 and HLA-DR9). In other words, the peptides of the present invention may have an ability to induce Th1 cells that are restricted by two or more kinds of MHC class II molecules. In another embodiment, the peptides of the present invention include an amino acid sequence of a peptide having IMP-3-specific CTL inducibility. The typical examples of such peptides having IMP-3-specific CTL inducibility include peptides having an amino acid sequence of SEQ ID NO: 3 or 4.

Since the binding groove in an MHC class II molecule is open at both ends, MHC class II binding peptides are allowed to have flexibility in their length. The core binding motif for MHC class II molecule is composed of 9 amino acid residues, and MHC class II binding peptides generally have other amino acid residues flanking with the core binding motif. The number of flanking amino acid residues is not restricted. Thus, all amino acid residues of SEQ ID NO: 1 or 2 are not indispensable for binding an MHC class II molecule. Accordingly, the peptide of the present invention can be a peptide having ability to induce a Th1 cell, such peptide including an amino acid sequence selected from the group consisting of:
(a) an amino acid sequence having more than 9 contiguous amino acids from the amino acid sequence of SEQ ID NO: 1 or 2; and
(b) an amino acid sequence of (a) in which one, two or several amino acids are substituted, deleted, inserted, and/or added.

The length of an MHC class II binding peptides is generally 10-30 amino acids. In that the amino acid sequences of SEQ ID NO: 1 and 2 are composed of a part of the amino acid sequence of IMP-3 (SEQ ID NO: 6), the peptides of the present invention can be a following peptide of [1] to [5]:
[1] An isolated peptide having 10-30 amino acids in length and including a part of the amino acid sequence of SEQ ID NO: 6, wherein such peptide comprises an amino acid sequence selected from the group consisting of:
(a) a contiguous amino acid sequence having more than 9 amino acids in length selected from the amino acid sequence of SEQ ID NO: 1 or 2; and
(b) an amino acid sequence of (a) in which one, two or several amino acids are substituted, deleted, inserted, and/or added, wherein such peptide has ability to induce Th1 cell(s);
[2] The isolated peptide of [1], wherein the peptide or fragment thereof has abilities to bind at least two kinds of MHC class II molecules;
[3] The isolated peptide of [2], wherein the MHC class II molecules are selected from the group consisting of HLA-DR8, HLA-DR53, HLA-DR14, and HLA-DR9;
[4] The isolated peptide of any one of [1] to [3], wherein said peptide comprises an amino acid sequence of a peptide having IMP-3-specific cytotoxic T lymphocyte (CTL) inducibility; and
[5] The isolated peptide of [4], wherein said peptide comprises the amino acid sequence selected from the group consisting of:
(a) an amino acid sequence selected from the group consisting of SEQ ID NOs: 1 and 2; and
(b) an amino acid sequence of (a) in which one, two or several amino acids are substituted, deleted, inserted, and/or added.

Th1 cells induced by the peptide of the present invention are specific to IMP-3. Therefore, in some embodiments, the present invention provides peptides of less than 30 amino acid residues consisting of a partial amino acid sequence of the amino acid sequence of SEQ ID NO: 6, wherein the peptides comprise the amino acid sequence of SEQ ID NO: 1 or 2.

Generally, software programs presently available on the Internet, such as those described in Wang P et al. 2008. PLoS Comput Biol. 4(4):e1000048. 11:568; and Wang P et al. 2010. BMC Bioinformatics. can be used to calculate the binding affinities between various peptides and HLA antigens in silico. Binding affinity with HLA antigens can be measured as described, for example, in Nielsen M and Lund O. 2009. BMC Bioinformatics. 10:296; Nielsen M et al. 2007. BMC Bioinformatics. 8:238. Bui H H, et al. 2005. Immunogenetics. 57:304-314. Sturniolo T et al. 1999. Nat Biotechnol. 17(6):555-561 and Nielsen M et al. 2008. PLoS Comput Biol. 4(7)e1000107. Thus, the present invention encompasses peptides of IMP-3 which are determined to bind with HLA antigens identified using such known programs.

As described above, since MHC class II binding peptides have flexibility in their length, the amino acid sequence of SEQ ID NO: 1 or 2 can be optionally flanked with additional amino acid residues so long as the resulting peptide retains the requisite Th1 cell inducibility. Such peptides having Th1 cell inducibility are typically, less than about 30 amino acids, often less than about 29 amino acids, and usually less than about 28 or 27 amino acids. The particular amino acid sequence(s) flanking the amino acid sequence selected from among SEQ ID NOs: 1 and 2 are not limited and can be composed of any kind of amino acids, so long as such flanking amino acid sequences do not impair the Th1 cell inducibility of the original peptide. In typical embodiments, such flanking amino acid sequence(s) may be selected from among the amino acid sequence of SEQ ID NO: 6 adjacent to the amino acid sequence of SEQ ID NO: 1 or 2; however, the present invention is not limited thereto. As such, the present invention also provides peptides having Th1 cell inducibility and an amino acid sequence selected from among SEQ ID NOs: 1 and 2.

On the other hand, since a core binding motif for an MHC class II molecule is composed of 9 amino acid residues, the full length of the amino acid sequence of SEQ ID NO: 1 or 2 is not indispensable for binding an MHC class II molecule and induction of Th1 cells. Thus, a peptide of the present invention can take the form of a peptide having more than 9 contiguous amino acids from the amino acid sequence of SEQ ID NO: 1 or 2, provided said peptide retains the requisite Th1 cell inducibility. Peptides having Th1 cell inducibility are typically, more than about 10 amino acids, often more than 11 or 12 amino acids, and usually more than 13 or 14 amino acids. Accordingly, the peptides of the present invention can be peptides having Th1 cell inducibility and an amino acid sequence having more than 9, 10, 11, 12, 13 or 14 contiguous amino acids from the amino acid sequence of SEQ ID NO: 1 or 2.

It is generally known that the modification of one, two, or more amino acids in a protein will not influence the function of the protein, and in some cases will even enhance the desired function of the original protein. In fact, modified peptides (i.e., peptides composed of an amino acid sequence in which one, two or several amino acid residues have been modified (i.e., substituted, added, deleted or inserted) as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention may have both Th1 cell inducibility and an amino acid sequence selected from among SEQ ID NO: 1 and 2, wherein one, two or even more amino acids are added, inserted, deleted and/or substituted. Alternatively, the peptides of the present invention may have both of Th1 cell inducibility and an amino acid sequence in which one, two or several amino acids are added, inserted, deleted and/or substituted in the amino acid sequence of SEQ ID NO: 1 or 2.

Those of skilled in the art recognize that individual additions or substitutions to an amino acid sequence which alter a single amino acid or a small percentage of amino acids tend to result in the conservation of the properties of the original amino acid side-chain. As such, they are often referred to as "conservative substitutions" or "conservative modifications", wherein the alteration of a protein results in a modified protein having a function analogous to the original protein. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be the peptides of the present invention. However, the peptides of the present invention are not restricted thereto and can include non-conservative modifications, so long as the modified peptide retains the Th1 cell inducibility of the original peptide. Furthermore, modified peptides should not exclude Th1 cell inducible peptides of polymorphic variants, interspecies homologues, and alleles of IMP-3.

To retain the requisite Th1 cell inducibility, one can modify (insert, add, deletion and/or substitute) a small number (for example, 1, 2 or several) or a small percentage of amino acids. Herein, the term "several" means 5 or fewer amino acids, for example, 4 or 3 or fewer. The percentage of amino acids to be modified is preferably 20% or less, more preferably, 15% of less, even more preferably 10% or 8%, less or 1 to 5%.

Homology analysis of preferred peptides of the present invention, namely SEQ ID NOs: 1 and 2 (IMP-$3_{402\text{-}423}$-LP, IMP-$3_{507\text{-}527}$-LP), confirm that these peptides do not have significant homology with peptides derived from any other known human gene products. Thus, the possibility of these peptides generating unknown or undesired immune responses when used for immunotherapy is significantly lowered. Accordingly, these peptides are expected to be highly useful for eliciting immunity in cancer patients against IMP-3.

When used in the context of immunotherapy, the peptides of the present invention or fragment thereof should be presented on the surface of an antigen presenting cell, preferably as a complex with an HLA class II antigen. Therefore, it is preferable to select peptides that not only induce Th1 cells but also possess high binding affinity to the HLA class II antigen. To that end, the peptides can be modified by substitution, insertion, deletion and/or addition of the amino acid residues to yield a modified peptide having improved binding affinity.

The present invention also contemplates the addition of one to two amino acids to the N and/or C-terminus of the described peptides. Such modified peptides having high HLA antigen binding affinity and retained Th1 cell inducibility are also included in the present invention.

For example, the present invention provides an isolated peptide of less than 31, 30, 29, 28, 27, or 26 amino acids in length which binds an HLA class II antigen, has Th1 cell inducibility, and comprises the amino acid sequence in which one, two or several amino acid(s) are modified in the amino acid sequence selected from the group consisting of SEQ ID NOs:1 and 2.

These peptides may also be processed in an APC to present a processed fragment thereon, when these peptides are contacted with, or introduced into APC. For example, the peptide of the present invention may be processed into a fragment composed of usually 11-26 (typically 15-25) amino acid residues to be presented on a surface of an APC.

However, when the peptide sequence is identical to a portion of the amino acid sequence of an endogenous or exogenous protein having a different function, negative side effects such as autoimmune disorders and/or allergic symptoms against specific substances may be induced. Therefore, it may be desirable to first perform homology searches using available databases to avoid situations in which the sequence of the peptide matches the amino acid sequence of another protein. When it becomes clear from the homology searches that no peptide identical to or having 1 or 2 amino acid differences as compared to the objective peptide exists in nature, the objective peptide can be modified in order to increase its binding affinity with HLA antigens, and/or increase its Th1 cell and/or CTL inducibility without any danger of such side effects.

Although peptides having high binding affinity to the HLA class II antigens as described above are expected to be highly effective, the candidate peptides, which are selected according to the presence of high binding affinity as an indicator, are further examined for the presence of Th1 cell inducibility. Herein, the phrase "Th1 cell inducibility" indicates an ability of a peptide to confer an ability to induce a Th1 cell on an APC when contacted with the APC. Further, "Th1 cell inducibility" includes the ability of the peptide to induce Th1 cell activation and/or Th1 cell proliferation, promote Th1 cell mediated-cytokines production including IFN-gamma production to help and/or stimulate other cells (e.g. CTL, macrophage).

Confirmation of Th1 cell inducibility is accomplished by inducing antigen-presenting cells carrying human MHC antigens (for example, B-lymphocytes, macrophages, and dendritic cells (DCs)), or more specifically DCs derived from human peripheral blood mononuclear leukocytes, and after stimulation with the peptides, mixing with CD4-positive T cells ($CD4^+$ T cells), and then measuring the IFN-gamma produced and released by $CD4^+$ T cells. Alternatively, Th1 cell inducibility of the peptide can be assessed based on CTL activation by Th1 cells. For example, $CD4^+$ T cells are co-cultured with DCs stimulated with a test peptide, and then mixing with CTLs and target cells for CTLs. The target cells can be radiolabeled with $^{51}Cr$ and such, and cytotoxic activity of CTLs activated by the cytokines secreted from Th1 cells can be calculated from radioactivity released from the target cells. Alternatively, Th1 cells inducibility can be assessed by measuring IFN-gamma produced and released by Th1 cells in the presence of antigen-presenting cells (APCs) stimulated with a test peptide, and visualizing the inhibition zone on the media using anti-IFN-gamma monoclonal antibodies.

In addition to the above-described modifications, the peptides of the present invention can also be linked to other substances, so long as the resulting linked peptide retains the Th1 cell inducibility of the original peptide. Examples of suitable substances include, for example: peptides, lipids, sugar and sugar chains, acetyl groups, natural and synthetic polymers, etc. The peptides of the present invention can contain modifications such as glycosylation, side chain oxidation, or phosphorylation, etc., provided the modifications do not destroy the biological activity of the original peptide. These kinds of modifications can be performed to confer additional functions (e.g., targeting function, and delivery function) or to stabilize the peptide.

For example, to increase the in vivo stability of a peptide, it is known in the art to introduce D-amino acids, amino acid mimetics or unnatural amino acids; this concept can also be adapted to the peptides of the present invention. The stability of a peptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

The peptides of the present invention may be presented on the surface of an APC as complexes in combination with HLA class II antigens and then induce Th1 cells. Therefore, the peptides forming complexes with HLA class II antigens on the surface of an APC are also included in the present invention. The APCs presenting the peptides of the present invention can be inoculated as vaccines.

The type of HLA antigens contained in the above complexes must match that of the subject requiring treatment and/or prevention. For example, in the Japanese population, HLA-DR8, HLA-DR53, HLA-DR14, and HLA-DR9 are prevalent and therefore would be appropriate for treatment of a Japanese patient. Typically, in the clinic, the type of HLA antigen of the patient requiring treatment is investigated in advance, which enables the appropriate selection of peptides having binding ability to the particular HLA class II antigen. In preferred embodiments, the peptides of the present invention can induce Th1 cells in a promiscuous manner. Herein, when a peptide can induce Th1 cells restricted by at least two different kinds of MHC class II molecules, the Th1 cell inducibility of the peptide is "promiscuous". In other word, when a peptide is recognized by at least two different kinds of MHC class II molecules, such antigen recognition is deemed "promiscuous". When used in the context of peptides, the phrase "recognized by at least two different kinds of MHC class II molecules" indicates that the peptide or fragment thereof can bind at least two different kinds of MHC class II molecules. For example, IMP-$3_{402-423}$-LP (SEQ ID NO: 1) is recognized by HLA-DR8, HLA-DR14 and HLA-DR53, and IMP-$3_{507-527}$-LP (SEQ ID NO: 2) is recognized by HLA-DR9 and HLA-DR14. Therefore, these peptides are typical examples of "promiscuous" epitope.

When using HLA-DR8, HLA-DR14 or HLA-DR53 positive APCs, the peptides having the amino acid sequence of SEQ ID NO: 1 are preferably used. When using HLA-DR9 or HLA-DR14 positive APCs, the peptides having the amino acid sequence of SEQ ID NO: 2 are preferably used.

Accordingly, in preferred embodiments, peptides having the amino acid sequence of SEQ ID NO: 1 may be used for the induction of Th1 cells in a subject that has been identified as having HLA-DR8, HLA-DR14 or HLA-DR53 prior to the induction. Likewise, peptides having the amino acid sequence of SEQ ID NO: 2 may be used for the induction of Th1 cells in a subject that has been identified as having HLA-DR9 or HLA-DR14 prior to the induction.

III. Preparation of IMP-3 Peptides

The peptides of the present invention can be prepared using well known techniques. For example, the peptides of the present invention can be prepared synthetically, using recombinant DNA technology or chemical synthesis. The peptide of the present invention can be synthesized individually or as longer polypeptides composed of two or more peptides. The peptides of the present invention can be then be isolated, i.e., purified, so as to be substantially free of other naturally occurring host cell proteins and fragments thereof, or any other chemical substances.

The peptides of the present invention may contain modifications, such as glycosylation, side chain oxidation, or phosphorylation; provided the modifications do not destroy the biological activity of the original reference peptides. Other illustrative modifications include incorporation of D-amino acids or other amino acid mimetics that can be used, for example, to increase the serum half life of the peptides.

Peptides of the present invention can be obtained through chemical synthesis based on the selected amino acid sequence. Examples of conventional peptide synthesis methods that can be adapted for the synthesis include:
(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the peptides of the present invention can be obtained adapting any known genetic engineering method for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide of the present invention can also be produced in vitro adopting an in vitro translation system.

IV. Polynucleotides

The present invention also provides a polynucleotide which encodes any of the aforementioned peptides of the present invention. These include polynucleotides derived from the natural occurring IMP-3 gene (GenBank Accession No. NM_006547.2 (SEQ ID NO: 5)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. As is well known in the art, a DNA is suitably composed of bases such as A, T, C, and G, and T is replaced by U in an RNA. One of skill will recognize that non-naturally occurring bases may be included in polynucleotides, as well.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5.

V. Antigen-Presenting Cells (APCs)

The present invention also provides antigen-presenting cells (APCs) that present complexes formed between HLA class II antigens and the peptides of the present invention or fragment thereof on its surface. The APCs that are obtained by contacting the peptides of the present invention can be derived from patients who are subject to treatment and/or prevention, and can be administered as vaccines by themselves or in combination with other drugs including the peptides of the present invention, Th1 cells or CTLs.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since a DC is a representative APC having the strongest Th1 cell-inducing activity among APCs, DCs find use as the APCs of the present invention.

Moreover, in preferred embodiments, the peptides of the present invention can also induce CTL response mediated with the MHC class I antigen, as well as Th1 (class-II). In general, it is well known that the length of epitope recognized by the MHC-class I antigen is shorter (e.g. 8-10 amino acid residues) than that of MHC-class II (15 or more).

Therefore, a processed product of the peptide of the present invention leads to induce CTL. In fact, CTL induced from IMP-3$_{507\text{-}527}$-LP (SEQ ID NO: 2) recognizes the fragment (KTVNELQNL: SEQ ID NO: 3) and the fragment (NLS-SAEVVV: SEQ ID NO: 4) which has already been identified as a CTL recognition epitope. Accordingly, peptides of the present invention induce not only Th1 but also CTL after processing of them in APCs. In other words, APCs contacted with the peptides of the present invention process them to present fragments thereof with MHC-class I antigens, as well as the whole of them presented with MHC-class-II antigens. Consequently, both of Th1 which recognizes the peptides of the present invention presented on APCs with the MHC class II antigen, and CTL induced via processed fragments of the peptide can be induced by using the peptides present invention.

For example, an APC can be obtained by inducing DCs from peripheral blood monocytes and then contacting (stimulating) them with the peptides of the present invention in vitro, ex vivo or in vivo. When the peptides of the present invention are administered to the subjects, APCs that present the peptides of the present invention or fragments thereof are induced in the body of the subject. Herein, the phrase "inducing an APC" includes contacting (stimulating) an APC with the peptides of the present invention to present complexes formed between HLA class II antigens and the peptides of the present invention or fragments thereof on their surface. Alternatively, after introducing the peptides of the present invention to APCs to allow the APCs to present the peptides or fragments thereof, the APCs can be administered to the subject as a vaccine. For example, the ex vivo administration can include steps of:

a: collecting APCs from a first subject,
b: contacting the APCs of step a, with the peptide of the present invention and
c: administering the peptide-loaded APCs to a second subject.

The first subject and the second subject may be the same individual, or can be different individuals. Alternatively, according to the present invention, use of the peptides of the present invention for manufacturing a pharmaceutical composition inducing antigen-presenting cells is provided. In addition, the present invention provides a method or process for manufacturing a pharmaceutical composition inducing antigen-presenting cells, wherein the method comprises the step for admixing or formulating the peptide of the present invention with a pharmaceutically acceptable carrier. Further, the present invention also provides the peptides of the present invention for inducing antigen-presenting cells. The APCs obtained by step (b) can be administered to the subject as a vaccine.

In one aspect of the present invention, the APCs of the present invention have a high level of Th1 cell inducibility. Herein, in the phrase "high level of Th1 cell inducibility", the high level is relative to the level of that by APCs contacting with no peptide or peptides which can not induce Th1 cells. Herein, when used in the context of APCs, the phrase "Th1 cell inducibility" indicates an ability of an APC to induce a Th1 cell when contacted with a CD4$^+$ T cell. Such APCs having a high level of Th1 cell inducibility can be prepared by a method which includes the step of transferring genes containing polynucleotides that encode the peptides of the present invention to APCs in vitro. The introduced genes can be in the form of DNAs or RNAs. Examples of methods for introduction include, without particular limitations, various methods conventionally performed in this field, such as lipofection, electroporation, and calcium phosphate method can be used. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present peptides. Alternatively, the APCs of the present invention can be prepared by a method which induces the step of contacting APCs with the peptide of the present invention.

In preferred embodiments, the APCs of the present invention can be APCs that present complexes of an MHC class II molecule selected from the group among HLA-DR8, HLA-DR14 and HLA-DR53 and the peptide of the present invention (including an amino acid sequence of SEQ ID NO: 1) on their surface. In another embodiment, the APCs of the present invention can be APCs that present complexes of an MHC class II molecule of HLA-DR9 and HLA-DR14 and the peptide of the present invention (including an amino acid sequence of SEQ ID NO: 2) on their surface. Preferably, HLA-DR8, HLA-DR53, HLA-DR14 and HLA-DR9 may be HLA-DRB1*0803, HLA-DRB4*0103, HLA-DRB*14:05 and HLA-DRB1*0901, respectively.

VI. T Helper Type 1 Cells (Th1 Cells)

A Th1 cell induced against any of the peptides of the present invention strengthens immune responses of any of effector cells including CTLs targeting cancer cells in vivo, and thus serve as vaccines, in a fashion similar to the peptides per se. Thus, the present invention also provides isolated Th1 cells that are specifically induced or activated by any of the peptides of the present invention.

Such Th1 cells can be obtained by (1) administering one or more peptides of the present invention to a subject, collecting Th1 cells from the subject, (2) contacting (stimulating) APCs and CD4$^+$ T cells, or peripheral blood mononuclear leukocytes in vitro with the peptides of the present invention, and then isolating Th1 cells, (3) contacting CD4$^+$ T cells or peripheral blood mononuclear leukocytes in vitro with the APCs of the present invention, or (4) introducing a polynucleotide encoding both of T cell receptor (TCR) subunits or polynucleotides encoding each of TCR subunits into a CD4$^+$ T cell, wherein the TCR can bind to a complex of an MHC class II molecule and the peptide of the present invention. Such APCs for the method of (3) can be prepared by the methods described above. Details of the method of (4) are described bellow in section "VII. T Cell Receptor (TCR)".

The Th1 cells that have been induced by stimulation with APCs of the present invention can be derived from patients who are subject to treatment and/or prevention, and can be administered by themselves or in combination with other drugs including the peptides of the present invention for the purpose of regulating effects. The obtained Th1 cells can activate and/or stimulate immune cells responsible for cellular immunity (e.g., CTL, macrophage). Such immune cells that can be activated by the Th1 cells of the present invention include CTLs that show cytotoxicity against target cells such as cancer cells. For example, target cells for such CTLs may be cells that endogenously express IMP-3 (e.g., cancer cells), or cells that are transfected with the IMP-3 gene. In preferred embodiments, the peptides of the present invention can contain at least one amino acid sequence of a CTL epitope peptide and also induce CTLs against IMP-3 expressing cells such as cancer cells, in addition to Th1 cells. In this case, the peptide of the present invention can induce Th1 cells and CTLs simultaneously or sequentially in vivo, and the induced Th1 cells can effectively activate the induced CTLs. Accordingly, such peptides containing at least one amino acid sequence of a CTL epitope peptide are suitable peptides for cancer immunotherapy.

Furthermore, the Th1 cells of the present invention secrete various cytokines (e.g. IFN-gamma) which activate and/or stimulate any CTLs against other target cells in an antigen independent manner. Accordingly, the Th1 cells of the present invention can also contribute to enhance CTL activity targeting cells expressing a tumor associated antigen (TAA) other than IMP-3. Thus, the Th1 cells of the present invention are useful for immunotherapy for not only tumor expressing IMP-3, but also tumor expressing other TAAs, as well as the peptides and APCs of the present invention.

In some embodiments, the Th1 cells of the present invention are Th1 cells that recognize cells presenting complexes of an HLA-DR or HLA-DP antigen and the peptide of the present invention. In the context of Th1 cells, the phrase "recognize a cell" refers to binding of a complex of an MHC class II molecule and the peptide of the present invention on the cell surface via its TCR and being activated in an antigen specific manner. Herein, the phrase "activated in antigen specific manner" refers to being activated in response to a particular MHC class II molecule and peptide and cytokine production from the activated Th1 cells are induced. In preferred embodiments, HLA-DR may be selected from the group consisting of HLA-DR8, HLA-DR53, HLA-DR14, and HLA-DR9. Preferably, HLA-DR8, HLA-DR53, and HHLA-DR9 may be HLA-DRB1*0803, HLA-DRB4*0103, HLA-DRB*14:05 and HLA-DRB1*0901, respectively.

VII. T Cell Receptor (TCR)

The present invention also provides a composition containing one or more polynucleotides encoding one or more polypeptides that are capable of forming a subunit of a T cell receptor (TCR), and methods of using the same. Such TCR subunits have the ability to form TCRs that confer specificity to CD4+ T cells against APCs presenting IMP-3 peptides. By using the known methods in the art, the nucleic acids of alpha- and beta-chains as the TCR subunits of Th1 cells induced by the peptides of the present invention can be identified (WO2007/032255 and Morgan et al., J Immunol, 171, 3288 (2003)). The derivative TCRs can bind APCs displaying IMP-3 peptides with high avidity, and optionally mediate efficient cytokine productions.

The polynucleotide/polynucleotides encoding the TCR subunits (i.e., a single polynucleotide encoding both of the TCR subunits or multiple polynucleotides each encoding a separate TCR subunits) can be incorporated into suitable vectors e.g. retroviral vectors. These vectors are well known in the art. The polynucleotides or the vectors containing them usefully can be transferred into a CD4+ T cell, for example, a CD4+ T cell from a patient. Advantageously, the present invention provides an off-the-shelf composition allowing rapid modification of a patient's own T cells (or those of another mammal) to rapidly and easily produce modified T cells having excellent cancer cell killing properties.

The present invention further provides Th1 cells which are prepared by transduction with the polynucleotide encoding both of the TCR subunits or polynucleotides encoding each of TCR subunits, wherein the TCR subunit can bind to the IMP-3 peptide (e.g. SEQ ID NO: 1 in the context of HLA-DR8, HLA-DR14 or HLA-DR53, SEQ ID NO: 2 in the context of HLA-DR9 or HLA-DR14). The transduced Th1 cells are capable of homing to cancer cells in vivo, and can be expanded by well known culturing methods in vitro (e.g., Kawakami et al., J Immunol., 142, 3452-3461 (1989)). The Th1 cells prepared as described above can be used to form an immunogenic composition useful in treating or the prevention of cancer in a patient in need of therapy or protection.

VIII. Pharmaceutical Agents or Compositions

To the extent that the methods and compositions of the present invention find utility in the context of the "treatment" of cancer, a treatment is deemed "efficacious" if it leads to clinical benefit such as, reduction in expression of IMP-3 gene, or a decrease in size, prevalence, or metastatic potential of the cancer in the subject. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis include a wide range of prophylactic therapies aimed at alleviating the severity of the particular disorder, e.g. reducing the proliferation and metastasis of tumors, reducing angiogenesis.

In the context of the present invention, the treatment and/or prophylaxis of cancer and/or the prevention of post-operative recurrence thereof include any of the following steps, such as surgical removal of cancer cells, inhibition of the growth of cancerous cells, involution or regression of a tumor, induction of remission and suppression of occurrence of cancer, tumor regression, and reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effective treatment and/or prophylaxis, including 10%, 20%, 30% or more reduction, or stable disease.

As described above, the Th1 cells induced by the peptides of the present invention can help immune cells responsible for cellular immunity. Such immune cells include CTLs against not only cancer cells expressing IMP-3, but also cancer cells expressing other TAAs, since cytokines secreted by Th1 cells can affect CTLs in antigen independent manner. Accordingly, the present invention provides a pharmaceutical agent or composition comprising at least one peptide of the present invention. In the pharmaceutical agent or composition, such peptide is present in a therapeutically or pharmaceutically effective amount.

A pharmaceutical agent or composition of the present invention is useful for helping, stimulating and/or enhancing any immune cells responsible for cellular immunity (e.g., CTLs, macrophage), since Th1 cells induced by the agent or composition of the present invention can secrete cytokines that affects any immune cells responsible for cellular immunity. Therefore, the agent or composition of the present invention is useful for any purposes of enhancing or promoting immune responses mediated with such immune cells including CTLs. For example, the present invention provides agent or compositions comprising at least one of the peptide of the present invention, for use in treatment and/or prevention of cancer since the agent or composition of the present invention can enhance or promote immune responses against cancer or tumor mediated with such immune cells. The amount of the peptide in such agent or composition may be an amount that is effective in significantly enhancing or stimulating immunological response in a subject carrying a cancer expressing IMP-3.

The present invention also provides an agent or composition for enhancing or stimulating immunological responses mediated with an MHC class I antigen, such as HLA-A2 and HLA-A24. In another embodiment, the present invention further provides a use of the peptide of the present invention for manufacturing an agent or composition for enhancing or stimulating an immunological response mediated with an MHC class I antigen.

In preferred embodiments, IMP-3 derived peptides identified in the course of the present invention can induce Th1 cells, as well as CTLs against IMP-3-expressing cells. Accordingly, the present invention also provides agents or compositions comprising at least one of the peptide of the present invention, for use in the induction of CTLs against cancer or tumor expressing IMP-3.

Moreover, the agent or composition comprising at least one of the peptides of the present invention can be used in enhancing or promoting immune responses mediated by MHC class II molecules.

Since IMP-3 expression is specifically elevated in several cancer types, including bladder cancer, cervical cancer, cholangiocellular carcinoma, chronic myelocytic leukemia, colon cancer, rectum cancer, esophageal cancer, gastric diffuse-type cancer, non-small-cell lung cancer (NSCLC), small-cell lung cancer (SCLC), lymphoma, osteosarcoma, ovarian cancer, renal carcinoma, soft tissue tumor, testicular tumor, and HNC, as compared with normal tissue (WO2004/031413, WO2007/013665, WO2007/013671, Tomita Y, et al., Cancer Sci 2011; 102:71-8, and our microarray data (data not shown)), the peptides of the present invention or polynucleotides encoding the peptides can be used for the treatment and/or prophylaxis of cancer or tumor, and/or for the prevention of postoperative recurrence thereof. Thus, the present invention provides a pharmaceutical agent or a composition for treating and/or for the prophylaxis of cancer or tumor, and/or prevention of postoperative recurrence thereof, which comprises one or more of the peptides of the present invention, or polynucleotides encoding the peptides as an active ingredient. Alternatively, the present peptides can be expressed on the surface of any of the foregoing cells, such as APCs for the use as pharmaceutical agents or compositions. In addition, the aforementioned Th1 cells can also be used as active ingredients of the present pharmaceutical agents or compositions.

In another embodiment, the present invention also provides the use of an active ingredient selected from among:

(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention
in manufacturing a pharmaceutical composition or agent for treating cancer or tumor.

Alternatively, the present invention further provides an active ingredient selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention
for use in treating cancer or tumor.

Alternatively, the present invention further provides a method or process for manufacturing a pharmaceutical composition or agent for treating cancer or tumor, wherein the method or process includes the step of formulating a pharmaceutically or physiologically acceptable carrier with an active ingredient selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention
as active ingredients.

In another embodiment, the present invention also provides a method or process for manufacturing a pharmaceutical composition or agent for treating cancer or tumor, wherein the method or process includes the step of admixing an active ingredient with a pharmaceutically or physiologically acceptable carrier, wherein the active ingredient is selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention.

Alternatively, the pharmaceutical composition or agent of the present invention may be used for either or both of the prophylaxis of cancer or tumor and prevention of postoperative recurrence thereof.

The present pharmaceutical agents or compositions find use as a vaccine. In the context of the present invention, the phrase "vaccine" (also referred to as an immunogenic composition) refers to a composition that has the function to induce anti-tumor immunity upon inoculation into animals.

The pharmaceutical agents or compositions of the present invention can be used to treat and/or prevent cancers or tumors, and/or prevent postoperative or metastatic recurrence thereof in subjects or patients. Examples of such subjects include humans as well as other mammals including, but not limited to, mouse, rat, guinea-pig, rabbit, cat, dog, sheep, goat, pig, cattle, horse, monkey, baboon, and chimpanzee, particularly a commercially important animal or a domesticated animal.

In the course of the present invention, the peptides having an amino acid sequence selected from among SEQ ID NOs: 1 and 2 have been found to be promiscuous Th1 cell epitopes restricted by several HLA-DR and/or HLA-DP molecules (e.g., HLA-DR8, HLA-DR53, HLA-DR9, HLA-DR14) and can be candidates that can induce potent and specific immune response against cancer due to immune responses mediated with MHC class II molecules. Therefore, the present pharmaceutical agents or compositions which include any of these peptides having the amino acid sequences of SEQ ID NOs: 1 or 2 are particularly suited for the administration to subjects that have at least one selected from among HLA-DR8, HLA-DR53, HLA-DR14, and HLA-DR9 as an MHC class II molecule. The same applies to pharmaceutical agents or compositions which contain polynucleotides encoding any of these peptides.

Alternatively, in preferred embodiments, a peptide identified in the course of the present invention can also induce CTLs specific to IMP-3, when the peptide is applied to a subject having HLA-A2 or HLA-A24. Accordingly, through the administration of the peptide of the present invention, it is further expected that CTL response against cancer expressing IMP-3 can be induced in addition to Th1 cell induction. Moreover, the peptide of the present invention can not only induce CTL response against IMP-3-expressing cells via processing thereof, but also enhance it by Th1 cell induction mediated thereby. Accordingly, in order to achieve inductions of both of Th1 cells and IMP-3-specific CTLs in the same subject, for example, the subject to be treated preferably has HLA-DR9 or HLA-DR14 as an MHC class II molecule and HLA-A24 or HLA-A2 as an MHC class I molecule, when administering peptides having the amino acid sequence of SEQ ID NO:2.

In another embodiment, the present invention provides an immunological cancer therapy dependent on Th1 cell induction. The therapeutic strategy provided by the present invention is applicable to and effective for any cancers independent of IMP-3 expression, as long as immune cells activated by cytokines secreted from Th1 cells target objective cancer cells.

Cancers or tumors to be treated by the pharmaceutical agents or compositions of the present invention include any kinds of cancers or tumors expressing IMP-3, including, but are not limited to, for example, bladder cancer, cervical cancer, cholangiocellular carcinoma, chronic myelocytic leukemia, colon cancer, rectum cancer, esophageal cancer, gastric diffuse-type cancer, non-small-cell lung cancer (NSCLC), small-cell lung cancer (SCLC), lymphoma, osteosarcoma, ovarian cancer, renal carcinoma, soft tissue tumor, testicular tumor, and HNC.

The present pharmaceutical agents or compositions can contain in addition to the aforementioned active ingredients, other peptides that have the ability to induce Th1 cells or CTLs, other polynucleotides encoding the other peptides, other cells that present the other peptides or fragment thereof, and the like. Examples of such "other" peptides having the ability to induce Th1 cells or CTLs include, but are not limited to, peptides derived from cancer specific antigens (e.g., identified TAAs), but are not limited thereto.

If necessary, the pharmaceutical agents or compositions of the present invention can optionally include other therapeutic substances as an additional active ingredient, so long as the substance does not inhibit the antitumoral effect of the active ingredient, e.g., any of the present peptides. For example, formulations can include antiinflammatory agents, pain killers, chemotherapeutics, and the like. In addition to including other therapeutic substances in the medicament itself, the medicaments of the present invention can also be administered sequentially or concurrently with the one or more other pharmacologic agents. The amounts of medicament and pharmacologic agent depend, for example, on what type of pharmacologic agent(s) is/are used, the disease being treated, and the scheduling and routes of administration.

Those of skill in the art will recognize that, in addition to the ingredients particularly mentioned herein, the pharmaceutical agents or compositions of the present invention can include other agents conventional in the art having regard to the type of formulation in question (e.g., fillers, binders, diluents, excipients, etc).

In one embodiment of the present invention, the present pharmaceutical agents or compositions can be included in articles of manufacture and kits containing materials useful for treating the pathological conditions of the disease to be treated, e.g., cancer. The article of manufacture can include a container of any of the present pharmaceutical agents or compositions with a label. Suitable containers include bottles, vials, and test tubes. The containers can be formed from a variety of materials, such as glass or plastic. The label on the container should indicate the agent is used for treating or prevention of one or more conditions of the disease. The label can also indicate directions for administration and so on.

In addition to the container described above, a kit including a pharmaceutical agent or composition of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical agents or compositions can, if desired, be packaged in a pack or dispenser device that can contain one or more unit dosage forms containing the active ingredient. The pack can, for example, include metal or plastic foil, such as a blister pack. The pack or dispenser device can be accompanied by instructions for administration.

(1) Pharmaceutical Agents or Compositions Containing the Peptides as the Active Ingredient:

The peptide of the present invention can be administered directly as a pharmaceutical agent or composition, or if necessary, that has been formulated by conventional formulation methods. In the latter case, in addition to the peptides of the present invention, carriers, excipients, and such that are ordinarily used for drugs can be included as appropriate without particular limitations. Examples of such carriers include, but are not limited to, sterilized water, physiological saline, phosphate buffer, culture fluid and such. Furthermore, the pharmaceutical agents or compositions can contain as necessary, stabilizers, suspensions, preservatives, surfactants and such. The pharmaceutical agents or compositions of the present invention can be used for anticancer purposes.

The peptides of the present invention can be prepared in a combination, composed of two or more of peptides of the present invention to induce Th1 cells in vivo. The peptide combination can take the form of a cocktail or can be conjugated to each other using standard techniques. For example, the peptides can be chemically linked or expressed as a single fusion polypeptide sequence. The peptides in the combination can be the same or different.

By administering the peptides of the present invention, the peptides or fragments thereof are presented at a high density by the HLA class II antigens on APCs, then Th1 cells that specifically react toward the complex formed between the displayed peptide and the HLA class II antigen are induced. Alternatively, APCs (e.g., DCs) are removed from subjects and then stimulated by the peptides of the present invention to obtain APCs that present any of the peptides of this invention or fragments thereof on their surface. These APCs can be readministered to the subjects to induce Th1 cells in the subjects, and as a result, aggressiveness towards the tumor-associated endothelium can be increased.

The pharmaceutical agents or compositions for the treatment and/or prevention of cancer or tumor that include a peptide of the present invention as the active ingredient, can also include an adjuvant known to effectively establish cellular immunity. Alternatively, the pharmaceutical agents or compositions can be administered with other active ingredients or can be administered by formulation into granules. An adjuvant refers to a compound that enhances the immune response against the protein when administered together (or successively) with the protein having immunological activity. Adjuvants contemplated herein include those described in the literature (Clin Microbiol Rev 1994, 7: 277-89). Examples of suitable adjuvants include, but are not limited to, aluminum phosphate, aluminum hydroxide, alum, cholera toxin, *salmonella* toxin, Incomplete Freund's adjuvant (IFA), Complete Freund's adjuvant (CFA), ISCO-Matrix, GM-CSF, CpG, O/W emulsion, and the like.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Examples of preferred salts include salts with an alkali metal, salts with a metal, salts with an organic base, salts with an organic acid (e.g., acetic acid, formic acid, propionic acid, fumaric acid, maleic acid, succinic acid, tartaric acid, citric acid, malic acid, oxalic acid, benzoic acid, methanesulfonic acid and so on) and salts with an inorganic acid (e.g., hydrochloric acid, phosphoric acid, hydrobromic acid, sulfuric acid and so on). As used herein, the phrase "pharmaceutically acceptable salt" refers to those salts that retain the biological effectiveness and properties of the compound and which are obtained by reaction with inorganic acids or bases such as hydrochloric acid, hydrobromic acid, sulfuric acid, nitric acid, phosphoric acid, methanesulfonic acid, ethanesulfonic acid, p-toluenesulfonic acid, salicylic acid and the like.

In some embodiments, the pharmaceutical agents or compositions of the present invention may further include a component which primes Th1 cells and optionally CTLs. Lipids have been identified as agents capable of priming Th1 cells and optionally CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of Th1 cell and optionally CTL responses, *E. coli* lipoproteins, such as tripalmitoyl-S-glycerylcysteinlyseryl-serine (P3CSS) can be used to prime Th1 cells and optionally CTLs when covalently attached to an appropriate peptide (see, e.g., Deres et al., Nature 1989, 342: 561-4).

Examples of suitable methods of administration include, but are not limited to, oral, intradermal, subcutaneous, intramuscular, intraosseous, peritoneal, and intravenous injection, or such, and systemic administration or local administration to the vicinity of the targeted sites (i.e., direct injection). The administration can be performed by single administration or boosted by multiple administrations. A pharmaceutically or therapeutically effective amount of the peptide of the present invention can be administered to a subject in need of treatment of cancer expressing IMP-3. Alternatively, an amount of the peptide of the present invention sufficient to enhance or stimulate immunological response mediated with Th1 cells, and/or to induce CTLs against cancer or tumor expressing IMP-3 can be administered to a subject carrying a cancer expressing IMP-3. The dose of the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 10 mg, for example, 0.5 mg to 5 mg, and can be administered once in a few days to few months. One skilled in the art can readily determine suitable and optimal dosages.

(2) Pharmaceutical Agents or Compositions Containing Polynucleotides as the Active Ingredient:

The pharmaceutical agents or compositions of the present invention can also contain polynucleotides encoding the peptides disclosed herein in an expressible form. Herein, the phrase "in an expressible form" means that the polynucleotide, when introduced into a cell, will be expressed in vivo as a polypeptide that induces anti-tumor immunity. In an illustrative embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922, 687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a subject can be either direct, in which case the subject is directly exposed to a polynucleotide-carrying vector, or indirect, in which case, cells are first transformed with the polynucleotide of interest in vitro, then the cells are transplanted into the subject. These two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, N Y, 1993; and Krieger, Gene Transfer and Expression, A Laboratory Manual, Stockton Press, N Y, 1990.

Like administration of peptides, administration of polynucleotides may be performed by oral, intradermal, subcutaneous, intravenous, intramuscular, intraosseous, and/or peritoneal injection, or such, and via systemic administration or local administration to the vicinity of the targeted sites finds use. The administration can be performed by single administration or boosted by multiple administrations. A pharmaceutically or therapeutically effective amount of the polynucleotide of the present invention can be administered to a subject in need of treatment of cancer expressing IMP-3. Alternatively, an amount of the polynucleotide of the present invention sufficient to enhance or stimulate immunological response mediated with Th1 cells, and/or to induce CTLs against cancer or tumor expressing IMP-3 can be administered to a subject carrying a cancer expressing IMP-3. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 10 mg, for example, 0.5 mg to 5 mg, and can be administered once every a few days to once every few months. One skilled in the art can readily determine suitable and optimal dosages.

IX. Methods Using the Peptides, APCs or Th1 Cells

The peptides of the present invention and polynucleotides encoding such peptides can be used for inducing APCs and Th1 cells of the present invention. The APCs of the present invention can be also used for inducing Th1 cells of the present invention. The peptides, polynucleotides, and APCs can be used in combination with any other compounds so long as the compounds do not inhibit their Th1 cell inducibility. Thus, any of the aforementioned pharmaceutical agents or compositions of the present invention can be used for inducing Th1 cells, and in addition thereto, those including the peptides and polynucleotides can be also used for inducing APCs as discussed below.

(1) Method of Inducing Antigen-Presenting Cells (APCs):

The present invention provides methods of inducing APCs using the peptides of the present invention or polynucleotides encoding the peptides. The induction of APCs can be performed as described above in section "V. Antigen-presenting cells". The present invention also provides a method for inducing APCs having Th1 cell inducibility, the induction of which has been also mentioned under the item of "V. Antigen-presenting cells", supra.

Alternatively, the present invention provides a method for preparing an antigen-presenting cell (APC) which has ability to induce a Th1 cell, wherein the method can include one of the following steps:

(a) contacting an APC with a peptide of the present invention in vitro, ex vivo or in vivo; and (b) introducing a polynucleotide encoding a peptide of the present invention into an APC.

Alternatively, the present invention provides methods for inducing an APC having Th1 cell inducibility, wherein the methods include the step selected from the group consisting of:

(a) contacting an APC with the peptide of the present invention, and (b) introducing the polynucleotide encoding the peptide of the present invention into an APC.

The methods of the present invention can be carried out in vitro, ex vivo or in vivo. Preferably, the methods of the present invention can be carried out in vitro or ex vivo. In preferred embodiment, APCs used for induction of APCs having Th1 cell inducibility can be preferably APCs expressing at least one selected from among HLA-DR8, HLA-DR53, HLA-DR14, and HLA-DR9 as an MHC class II molecule. Such APCs can be prepared by the methods well-known in the arts from peripheral blood mononuclear cells (PBMCs) obtained from a subject having at least one selected from among HLA-DR8, HLA-DR53, HLA-DR14, and HLA-DR9 as an MHC class II molecule. The APCs induced by the method of the present invention can be APCs that present a complex of the peptide of the present invention or fragment thereof and HLA class II antigen (e.g., HLA-DR8, HLA-DR53, HLA-DR9, HLA-DR14) on their surface. When APCs induced by the method of the present invention are administered to a subject in order to induce immune responses against cancer in the subject, the subject is preferably the same one from whom APCs are derived. However, the subject may be a different one from the APC donor so long as the subject has the same HLA type with the APC donor.

In another embodiment, the present invention provide agents or compositions for use in inducing an APC having Th1 cell inducibility, and such agents or compositions include one or more peptides or polynucleotides of the present invention.

In another embodiment, the present invention provides the use of the peptide of the present invention or the polynucleotide encoding the peptide in the manufacture of an agent or composition formulated for inducing APCs.

Alternatively, the present invention further provides the peptide of the present invention or the polypeptide encoding the peptide for use in inducing an APC having Th1 cell inducibility.

In preferred embodiments, the peptides of the present invention can induce not only Th1 response but also CTL response after processing them. Accordingly, in preferred embodiments, APCs prepared by the method of the present invention can be also useful for inducing CTLs against IMP-3 expressing cells, including cancer cells. For example, when induced by the peptides containing the amino acid sequence of SEQ ID NO: 4, APCs expressing HLA-A2 are suitable for inducing IMP-3-specific CTLs. Alternatively, when induced by the peptides containing the amino acid sequence of SEQ ID NO: 3, APCs expressing HLA-A24 are suitable for inducing IMP-3-specific CTLs.

(2) Method of Inducing Th1 Cells:

Furthermore, the present invention provides methods for inducing Th1 cells using the peptides of the present invention, polynucleotides encoding the peptides or APCs presenting the peptides of the present invention or fragments thereof. The present invention also provides methods for inducing Th1 cells using a polynucleotide encoding a polypeptide that is capable of forming a T cell receptor (TCR) subunit recognizing a complex of the peptides of the present invention and HLA class II antigens. Preferably, the methods for inducing Th1 cells comprise at least one step selected from the group consisting of:

a: contacting a CD4-positive T cell with an antigen-presenting cell that presents on its surface a complex of an HLA class II antigen and the peptide of the present invention or fragment thereof, and b: introducing a polynucleotide encoding both of TCR subunits or polynucleotides encoding each of TCR subunits, wherein the TCR can recognize or bind to a complex of the peptide of the present invention or fragment thereof and an HLA class II antigen, into a CD4-positive T cell.

When the peptides of the present invention are administered to a subject, Th1 cells are induced in the body of the subject, and immune responses mediated by MHC class II molecules (e.g., immune responses targeting cancer cells) are enhanced. Alternatively, the peptides and polynucleotides encoding the peptides can be used for an ex vivo therapeutic method, in which subject-derived APCs and CD4-positive cells, or peripheral blood mononuclear leukocytes are contacted (stimulated) with the peptides of the present invention in vitro, and after inducing Th1 cells, the activated Th1 cells are returned to the subject. For example, the method can include the steps of:

a: collecting APCs from subject,
b: contacting the APCs of step a, with the peptide of the present invention,
c: mixing the APCs of step b with $CD4^+$ T cells, and co-culturing for inducing Th1 cells: and
d: collecting $CD4^+$ T cells from the co-culture of step c.

Furthermore, Th1 cells can be induced by introducing a polynucleotide encoding both of TCR subunits or polynucleotides encoding each of TCR subunits, wherein the TCR can bind to a complex of the peptide of the present invention or fragment thereof and an HLA class II antigen, into CD4-positive T cells. Such transduction can be performed as described above in section "VII. T Cell Receptor (TCR)".

The methods of the present invention can be carried out in vitro, ex vivo or in vivo. Preferably, the methods of the present invention can be carried out in vitro or ex vivo. CD4 positive T cells used for induction of Th1 cells can be prepared by well-known methods in the art from PBMCs obtained from a subject. In preferred embodiments, the donor for CD4-positive T cells can be a subject having at least one selected from among HLA-DR8, HLA-DR53, HLA-DR14, and HLA-DR9 as an MHC class II molecule. The Th1 cells induced by the methods of the present invention can be Th1 cells that can recognize APCs presenting a complex of the peptide of the present invention or fragment thereof and HLA class II antigen on its surface. When Th1 cells induced by the method of the present invention are administered to a subject in order to induce immune responses against cancer in the subject (or immune responses mediated by MHC class I molecules), the subject is preferably the same one from whom CD4-positive T cells are derived. However, the subject may be a different one from the CD4-positive T cell donor so long as the subject has the same HLA type with the CD4-positive T cell donor.

In preferred embodiments, the peptides of the present invention can induce CTLs against IMP-3 expressing cells, as well as Th1 cells. Therefore, the present invention further provides a method for inducing a CTL, which comprises at least one step selected from the group consisting of:

a: co-culturing both of a CD4-positive T cell and a CD8-positive T cell with APCs contacted with the peptide of the present invention; and b: co-culturing a CD8-positive T cell with an APC contacted with the peptide of the present invention.

In such methods of inducing CTLs, the peptides of the present invention are processed in APCs to produce CTL epitope peptides, and produced CTL epitope peptides are presented on APC's surface.

Alternatively, according to the present invention, use of the peptides of the present invention for manufacturing a pharmaceutical agent or composition inducing Th1 cells is provided. In addition, the present invention provides a method or process for manufacturing a pharmaceutical agent or composition inducing Th1 cells, wherein the method comprises the step for admixing or formulating the peptide of the present invention with a pharmaceutically acceptable carrier. Further, the present invention also provides the peptide of the present invention for inducing Th1 cells.

The $CD4^+$ T cells induced by the method of the present invention can be administered to a subject as a vaccine.

In the context of the present invention, cancer overexpressing IMP-3 can be treated with these active ingredients. Examples of such cancers include, but are not limited to, bladder cancer, cervical cancer, cholangiocellular carcinoma, chronic myelocytic leukemia, colon cancer, rectum cancer, esophageal cancer, gastric diffuse-type cancer, non-small-cell lung cancer (NSCLC), small-cell lung cancer (SCLC), lymphoma, osteosarcoma, ovarian cancer, renal carcinoma, soft tissue tumor, testicular tumor, and HNC. Accordingly, prior to the administration of the vaccines or pharmaceutical compositions comprising the active ingredients, it is preferable to confirm whether the expression level of IMP-3 in the cancer cells or tissues to be treated is enhanced as compared with normal cells of the same organ. Thus, in one embodiment, the present invention provides a method for treating cancer (over)expressing IMP-3, which method may include the steps of:

i) determining the expression level of IMP-3 in cancer cells or tissue(s) obtained from a subject with the cancer to be treated;

ii) comparing the expression level of IMP-3 with normal control; and iii) administrating at least one component selected from the group consisting of (a) to (d) described above to a subject with cancer overexpressing IMP-3 compared with normal control.

Alternatively, the present invention may provide a vaccine or pharmaceutical composition that includes at least one component selected from the group consisting of (a) to (d) described above, for use in administrating to a subject having cancer overexpressing IMP-3. In other words, the present invention further provides a method for identifying a subject to be treated with a IMP-3 polypeptide of the present invention, such method including the step of determining an expression level of IMP-3 in subject-derived cancer cells or tissue(s), wherein an increase of the level compared to a normal control level of the gene indicates that the subject has cancer which may be treated with the IMP-3 polypeptide of the present invention. Methods of treating cancer of the present invention are described in more detail below.

Further, in preferred embodiments, the HLA type of a subject may be identified before administering the peptides of the present invention. For example, peptides having the amino acid sequence of SEQ ID NO: 1 are preferably administered to a subject identified as having HLA-DR8, HLA-DR14 or HLA-DR53. Alternatively, peptides having the amino acid sequence of SEQ ID NO: 2 are preferably administered to a subject identified as having HLA-DR9 or HLA-DR14.

Any subject-derived cell or tissue can be used for the determination of IMP-3-expression so long as it includes the objective transcription or translation product of IMP-3. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from tissue suspected to be cancerous. Further, if necessary, the cell may be purified from the obtained bodily tissues and fluids, and then used as the subjected-derived sample.

A subject to be treated by the present method is preferably a mammal. Exemplary mammals include, but are not limited to, e.g., human, non-human primate, mouse, rat, dog, cat, horse, and cow.

According to the present invention, the expression level of IMP-3 in cancer cells or tissues obtained from a subject is determined. The expression level can be determined at the transcription (nucleic acid) product level, using methods known in the art. For example, the mRNA of IMP-3 may be quantified using probes by hybridization methods (e.g., Northern hybridization). The detection may be carried out on a chip or an array. The use of an array is preferable for detecting the expression level of IMP-3. Those skilled in the art can prepare such probes utilizing the sequence information of IMP-3. For example, the cDNA of IMP-3 may be used as the probes. If necessary, the probes may be labeled with a suitable label, such as dyes, fluorescent substances and isotopes, and the expression level of the gene may be detected as the intensity of the hybridized labels.

Furthermore, the transcription product of IMP-3 (e.g., SEQ ID NO: 5) may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of IMP-3. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degree Centigrade lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degree Centigrade for short probes or primers (e.g., 10 to 50 nucleotides) and at least about 60 degree Centigrade for longer probes or primers. Stringent conditions may also be achieved with the addition of destabilizing agents, such as formamide.

Alternatively, the translation product may be detected for the diagnosis of the present invention. For example, the quantity of IMP-3 protein (SEQ ID NO: 6) may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, $F(ab')_2$, Fv, etc.) of the antibody may be used for the detection, so long as the fragment or modified antibody retains the binding ability to the IMP-3 protein. Methods to prepare these kinds of antibodies for the detection of proteins are well known in the art, and any method may be employed in the present invention to prepare such antibodies and equivalents thereof.

As another method to detect the expression level of IMP-3 gene based on its translation product, the intensity of staining may be measured via immunohistochemical analysis using an antibody against the IMP-3 protein. Namely, in this measurement, strong staining indicates increased presence/level of the protein and, at the same time, high expression level of IMP-3 gene.

The expression level of a target gene, e.g., the IMP-3 gene, in cancer cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time as the cancer cells, by using a sample(s) previously collected and stored from a subject/subjects whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of IMP-3 gene in samples from subjects whose disease states are known. Furthermore, the control level can be derived from a database of expression patterns from previously tested cells. Moreover, according to an aspect of the present invention, the expression level of IMP-3 gene in a biological sample may be compared to multiple control levels determined from multiple reference samples. It is preferred to use a control level determined from a reference sample derived from a tissue type similar to that of the subject-derived biological sample. Moreover, it is preferred to use the standard value of the expression levels of IMP-3 gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

When the expression level of IMP-3 gene is increased as compared to the normal control level, or is similar/equivalent to the cancerous control level, the subject may be diagnosed with cancer to be treated.

More specifically, the present invention provides a method of (i) diagnosing whether a subject has the cancer to be treated, and/or (ii) selecting a subject for cancer treatment, which method includes the steps of:

a) determining the expression level of IMP-3 in cancer cells or tissue(s) obtained from a subject who is suspected to have the cancer to be treated;

b) comparing the expression level of IMP-3 with a normal control level;

c) diagnosing the subject as having the cancer to be treated, if the expression level of IMP-3 is increased as compared to the normal control level; and d) selecting the subject for cancer treatment, if the subject is diagnosed as having the cancer to be treated, in step c).

Alternatively, such a method includes the steps of:

a) determining the expression level of IMP-3 in cancer cells or tissue(s) obtained from a subject who is suspected to have the cancer to be treated;

b) comparing the expression level of IMP-3 with a cancerous control level;

c) diagnosing the subject as having the cancer to be treated, if the expression level of IMP-3 is similar or equivalent to the cancerous control level; and d) selecting the subject for cancer treatment, if the subject is diagnosed as having the cancer to be treated, in step c).

In some embodiments, such a method may further comprise the step of identifying, after or before the steps a)-d) defined above, a subject having an HLA selected from the group consisting of HLA-DR8, HLA-DR9, HLA-DR14 and HLA-DR53. Cancer therapy according to the present invention is preferable for a subject that suffers from cancer overexpressing IMP-3 and has any one of HLA-DR8, HLA-DR9, HLA-DR14 and HLA-DR53. Methods for HLA typing are well known in the art. For example, PCR-based methods for typing HLA alleles are well known. Antibodies specific for each HLA molecule are also appropriate tools for identifying HLA types of a subject.

The present invention also provides a kit for determining a subject suffering from cancer that can be treated with the IMP-3 polypeptide of the present invention, which may also be useful in assessing and/or monitoring the efficacy of a particular cancer therapy, more particularly a cancer immunotherapy. Illustrative examples of suitable cancers include, but are not limited to, bladder cancer, cervical cancer, cholangiocellular carcinoma, chronic myelocytic leukemia, colon cancer, rectum cancer, esophageal cancer, gastric diffuse-type cancer, non-small-cell lung cancer (NSCLC), small-cell lung cancer (SCLC), lymphoma, osteosarcoma, ovarian cancer, renal carcinoma, soft tissue tumor, testicular tumor, and HNC. More particularly, the kit preferably includes at least one reagent for detecting the expression of the IMP-3 gene in a subject-derived cancer cell, such reagent being selected from the group of:

(a) a reagent for detecting an mRNA of the IMP-3 gene;
(b) a reagent for detecting the IMP-3 protein; and
(c) a reagent for detecting the biological activity of the IMP-3 protein.

Examples of reagents suitable for detecting an mRNA of the IMP-3 gene include nucleic acids that specifically bind to or identify the IMP-3 mRNA, such as oligonucleotides that have a complementary sequence to a portion of the IMP-3 mRNA. These kinds of oligonucleotides are exemplified by primers and probes that are specific to the IMP-3 mRNA. These kinds of oligonucleotides may be prepared based on methods well known in the art. If needed, the reagent for detecting the IMP-3 mRNA may be immobilized on a solid matrix. Moreover, more than one reagent for detecting the IMP-3 mRNA may be included in the kit.

On the other hand, examples of reagents suitable for detecting the IMP-3 protein include antibodies to the IMP-3 protein. The antibody may be monoclonal or polyclonal. Furthermore, any fragment or modification (e.g., chimeric antibody, scFv, Fab, F(ab')$_2$, Fv, etc.) of the antibody may be used as the reagent, so long as the fragment or modified antibody retains the binding ability to the IMP-3 protein. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the IMP-3 protein may be included in the kit.

The kit may contain more than one of the aforementioned reagents. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers include bottles, vials, and test tubes. The containers may be formed from a variety of materials, such as glass or plastic.

As an embodiment of the present invention, when the reagent is a probe against the IMP-3 mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of IMP-3 mRNA present in the sample. The detection sites may be configured in any suitably detectable shape and are typically in the shape of a bar or dot spanning the width of a test strip.

The kit of the present invention may further include a positive control sample or IMP-3 standard sample. The positive control sample of the present invention may be prepared by collecting IMP-3 positive samples and then assaying their IMP-3 levels. Alternatively, a purified IMP-3 protein or polynucleotide may be added to cells that do not express IMP-3 to form the positive sample or the IMP-3 standard sample. In the present invention, purified IMP-3 may be a recombinant protein. The IMP-3 level of the positive control sample is, for example, more than the cut off value.

X. Antibodies

The present invention further provides antibodies that bind to the peptide of the present invention. Preferred antibodies specifically bind to the peptide of the present invention and will not bind (or will bind weakly) to other peptides. Alternatively, antibodies bind to the peptide of the invention as well as the homologs thereof. Antibodies against the peptide of the invention can find use in cancer diagnostic and prognostic assays, as well as imaging methodologies. Similarly, such antibodies can find use in the treatment, diagnosis, and/or prognosis of other cancers, to the extent IMP-3 is also expressed or over-expressed in a cancer patient. Moreover, intracellularly expressed antibodies (e.g., single chain antibodies) may therapeutically find use in treating cancers in which the expression of IMP-3 is involved, examples of which include, but are not limited to, bladder cancer, cervical cancer, cholangiocellular carcinoma, chronic myelocytic leukemia, colon cancer, rectum cancer, esophageal cancer, gastric diffuse-type cancer, non-small-cell lung cancer (NSCLC), small-cell lung cancer (SCLC), lymphoma, osteosarcoma, ovarian cancer, renal carcinoma, soft tissue tumor, testicular tumor, and HNC.

The present invention also provides various immunological assay for the detection and/or quantification of IMP-3 protein (SEQ ID NO: 6) or fragments thereof including a polypeptide composed of amino acid sequences selected from among SEQ ID NOs: 1 and 2. Such assays may include one or more anti-IMP-3 antibodies capable of recognizing and binding a IMP-3 protein or fragments thereof, as appropriate. In the present invention, anti-IMP-3 antibodies binding to IMP-3 polypeptide preferably recognize a polypeptide composed of amino acid sequences selected from among SEQ ID NOs: 1 and 2, preferably to the exclusion of other peptides. The binding specificity of antibody can be confirmed with inhibition test. That is, when the binding between an antibody to be analyzed and full-length of IMP-3 polypeptide is inhibited under presence of any fragment polypeptides having an amino acid sequence selected from among SEQ ID NOs: 1 and 2, the antibody is deemed to "specifically bind" the fragment. In the context of the present invention, such immunological assays are performed within various immunological assay formats well known in the art, including but not limited to, various types of radioimmunoassays, immunochromatograph technique, enzyme-linked immunosorbent assays (ELISA), enzyme-linked immunofluorescent assays (ELIFA), and the like.

Related immunological but non-antibody assays of the invention may also include T cell immunogenicity assays (inhibitory or stimulatory) as well as MHC binding assays. In addition, immunological imaging methods capable of detecting cancers expressing IMP-3 are also provided by the invention, including, but not limited to, radioscintigraphic imaging methods using labeled antibodies of the present invention. Such assays can clinically find use in the detection, monitoring, and prognosis of IMP-3 expressing cancers, examples of which include, but are not limited to, bladder cancer, cervical cancer, cholangiocellular carcinoma, chronic myelocytic leukemia, colon cancer, rectum cancer, esophageal cancer, gastric diffuse-type cancer, non-small-cell lung cancer (NSCLC), small-cell lung cancer (SCLC), lymphoma, osteosarcoma, ovarian cancer, renal carcinoma, soft tissue tumor, testicular tumor, and HNC.

The present invention also provides antibodies that bind to a peptide of the invention. An antibody of the invention can be used in any form, such as monoclonal or polyclonal antibodies, and include antiserum obtained by immunizing an animal such as a rabbit with the peptide of the invention, all classes of polyclonal and monoclonal antibodies, human antibodies and humanized antibodies produced by genetic recombination.

A peptide of the invention used as an antigen to obtain an antibody may be derived from any animal species, but preferably is derived from a mammal such as a human, mouse, or rat, more preferably from a human. A human-derived peptide may be obtained from the nucleotide or amino acid sequences disclosed herein.

According to the present invention, complete and partial peptides of polypeptide of the present invention may serve as immunization antigens. Examples of suitable partial peptide include, for example, the amino (N)-terminal or carboxy (C)-terminal fragment of a peptide of the present invention.

Herein, an antibody is defined as a protein that reacts with either the full length or a fragment of a IMP-3 peptide. In a preferred embodiment, antibody of the present invention can recognize fragment peptides of IMP-3 having an amino acid sequence selected from among SEQ ID NOs: 1 and 2. Methods for synthesizing oligopeptide are well known in the arts. After the synthesis, peptides may be optionally purified prior to use as immunogen. In the present invention, the oligopeptide (e.g., 24- or 26 mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, though preferably the compatibility with parental cells used for cell fusion is taken into account. In general, animals of Rodentia, Lagomorpha or Primate family may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies for use in the context of the present invention, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, wherein a non-human animal is immunized with an antigen for preparing hybridoma, human lymphocytes such as those infected by EB virus may be immunized with a peptide, peptide expressing cells or their lysates in vitro. Then, the immunized lymphocytes may be fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas may then be subsequently transplanted into the abdominal cavity of a mouse and the ascites extracted. The obtained monoclonal antibodies can be purified by, for example, ammonium sulfate precipitation, a protein A or protein G column, DEAE ion exchange chromatography or an affinity column to which the peptide of the present invention is coupled. An antibody of the present invention can be used not only for purification and detection of a peptide of the present invention, but also as a candidate for agonists and antagonists of a peptide of the present invention.

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides for recombinant antibodies prepared as described above.

An antibody of the present invention may be a fragment of an antibody or modified antibody, so long as it binds to one or more of the peptides of the invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584; 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Examples of suitable chromatography techniques, with the exception of affinity chromatography, include, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence (IF) may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the peptide of the invention, by exposing the antibody of the invention to a sample assumed to contain the peptide of the invention, and detecting or measuring the immune complex formed by the antibody and the peptide.

Because the method of detection or measurement of the peptide according to the invention can specifically detect or measure a peptide, the method can find use in a variety of experiments in which the peptide is used.

XII. Vectors and Host Cells

The present invention also provides for vectors and host cells into which a nucleotide encoding the peptide of a present invention is introduced. A vector of the present invention finds utility as a carrier of nucleotides, especially a DNA, of the present invention in host cell, to express the peptide of the present invention, or to administer the nucleotide of the present invention for gene therapy.

When *E. coli* is selected as the host cell and the vector is amplified and produced in a large amount in *E. coli* (e.g., JM109, DH5 alpha, HB101 or XL1Blue), the vector should have an "ori" suitable for amplification in *E. coli* and a marker gene suited for selecting transformed *E. coli* (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use. For example, an expression vector to be expressed in *E. coli* should have the above characteristics to be amplified in *E. coli*. When *E. coli*, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the *E. coli* is the pelB signal sequence (Lei et al., J Bacteriol 169: 4379 (1987)). Means for introducing of the vectors into the target host cells include, for example, the calcium chloride method, and the electroporation method.

In addition to *E. coli*, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "*Pichia* Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells, such as CHO, COS or NIH3T3 cells, the vector should carry a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Hereinafter, the present invention is described in more detail with reference to specific Examples. However, while the following materials, methods and examples may serve to assist one of ordinary skill in making and using certain embodiments of the present invention, there are only intended to illustrate aspects of the present invention and thus in no way to limit the scope of the present invention. As one of ordinary skill in the art will readily recognize, methods and materials similar or equivalent to those described herein can be used in the practice or testing of the present invention.

EXAMPLES

Materials and Methods
Cell Lines
Mouse fibroblast cell lines (L-cells), genetically engineered to express DR4 (DRB1*04:05), L-DR4; DR8 (DRB1*08:03), L-DR8; DR9 (DRB1*09:01), L-DR9; DR15 (DRB1*15:02), L-DR15; DR53 (DRB4*01:03), L-DR53; or DP5 (DPB 1*05:01), L-DP5 were used as antigen-presenting cells (APCs). A transporter associated with antigen processing (TAP)-deficient and HLA-A2-positive cell line T2 was purchased from Riken Cell Bank (Tsukuba, Japan).

Prediction of HLA Class II-Binding Peptides

To predict potential promiscuous HLA-class II binding human IMP-3-derived peptides, the amino acid sequence of the human IMP-3 protein was analyzed by a recently developed computer algorithm (IEDB analysis resource, consensus method, tools.immuneepitope.org/analyze/html/mhc_II_binding.html) (Wang P, et al., BMC Bioinformatics 2010; 11:568; Wang P, et al., PLoS Comput Biol 2008; 4:e1000048). The program analyzed 15 amino-acid-long sequences offset to encompass the entire IMP-3 protein. The 22 and 21 amino-acid-long peptides, IMP-$3_{402-423}$-long peptide (LP) (QSETETVHLFIPALSVGAIIGK: SEQ ID NO: 1) and IMP-$3_{507-527}$-LP (GKTVNELQNLSSAEVVVPRDQ: SEQ ID NO: 2), with overlapping high consensus percentile ranks for multiple HLA-class II molecules encoded for by DRB1*09:01, DRB1*04:05 or DRB1*15:02 alleles, and that include IMP-3-derived 9-mer CTL epitopes (IMP-3-A$24_{508-516}$ and IMP-3-A$2_{515-523}$) were selected and synthesized (FIG. 1 and Table 1).

TABLE 1

Binding algorithm scores of IMP-3-derived peptides for HLA-class II molecules

| Amino acid residues position | Percentile Rank | | |
|---|---|---|---|
| | HLA-DR9 (DRB1*09:01) | HLA-DR4 (DRB1*04:05) | HLA-DR15 (DRB1*15:02) |
| IMP-$3_{402-423}$-LP | | | |
| 402-416 | 26.4 | 2.0 | 3.0 |
| 403-417 | 22.7 | 2.0 | 3.0 |
| 404-418 | 22.2 | 2.0 | 3.0 |
| 405-419 | 3.8 | 2.0 | 3.0 |
| 406-420 | 2.8 | 2.0 | 3.0 |
| 407-421 | 2.1 | 2.9 | 3.0 |
| 408-422 | 2.2 | 3.0 | 3.0 |
| 409-423 | 3.2 | 5.3 | 4.3 |
| IMP-$3_{507-527}$-LP | | | |
| 507-521 | 2.6 | 4.3 | 5.4 |
| 508-522 | 1.1 | 4.2 | 5.4 |
| 509-523 | 0.5 | 6.0 | 5.4 |
| 510-524 | 0.3 | 6.2 | 5.4 |
| 511-525 | 0.6 | 7.9 | 5.4 |
| 512-526 | 1.2 | 15.4 | 5.4 |
| 513-527 | 2.9 | 16.0 | 5.4 |

Peptide-binding algorithm scores for indicated HLA-class II molecules are shown for each 15-mer IMP-3-derived overlapping peptide.

Synthetic Peptides and Recombinant Proteins

Two human IMP-3-derived short peptides (SPs) presented by HLA-A2 (IMP-3-A$2_{515-523}$) (Tomita Y, et al., Cancer Sci 2011; 102:71-8) or HLA-A24 (IMP-3-A$24_{508-516}$) (Suda T, et al., Cancer Sci 2007; 98:1803-8), and two LPs (IMP-$3_{402-423}$-LP and IMP-$3_{507-527}$-LP) were synthesized (MBL, Nagoya, Japan; purity>95%; FIG. 1B). A human immunodeficiency virus (HIV)-SPs that bind to HLA-A2 (HIV-A2) was used as negative control SPs (Tomita Y, et al., Cancer Sci 2011; 102:71-8; Tomita Y, et al., Cancer Sci 2011; 102:697-705). Peptides were dissolved in dimethylsulfoxide at 10 micro-g/micro-L, and stored at −80 degrees C. The recombinant whole IMP-3 protein was purchased from ProSci Incorporated (California, USA; purity>90%). The recombinant human whole IMP-3 protein was expressed by *Escherichia coli* BL21 with a pET28a vector (Novagen) and the purified recombinant human IMP-3 protein was used as a control.

Generation of Antigen-Specific CD4$^+$ T-Cells from Healthy Donors

The research protocol for collecting and using PBMCs from healthy donors was approved by the Institutional Review Board of Kumamoto University. The present inventors obtained PBMCs from 4 healthy donors with written informed consents. Genotyping of HLA-A, DRB1, and DPB 1 alleles was performed at the HLA Laboratory (Kyoto, Japan) (Table 2). Induction of antigen-specific CD4$^+$ T-cells was performed as described previously, with some modifications (Zarour H M, et al., Cancer Res 2000; 60:4946-52). CD4$^+$ T-cells were purified from PBMCs by positive selection with magnetic microbeads (Miltenyi Biotec, Auburn, Calif., USA) (Inoue M, et al., Int J Cancer 2010; 127:1393-403). Monocyte-derived dendritic cells (DCs) were generated from CD14$^+$ cells by in vitro culture, as described previously (Harao M, et al., Int J Cancer 2008; 123:2616-25), and used as antigen-presenting cells (APCs) to induce antigen-specific CD4$^+$ T-cells. DCs ($1 \times 10^4$ cells/well) were pulsed with 10 micro-g/mL LP for 3 h and irradiated (45 Gy), then mixed with CD4$^+$ T-cells ($3 \times 10^4$ cells/well) in 200 micro-L AIM-V supplemented with 5% human decomplemented plasma in each well of a 96-well, flat-bottomed culture plate. After 7 days, half of the medium was removed from each culture, and fresh medium (100 micro-L/well) containing irradiated (50 Gy) autologous PBMCs ($1 \times 10^5$ cells/well) pulsed with peptide (10 micro-g/mL) and 5 ng/mL recombinant human interleukin 7 (rhIL-7) was added. Two days after the second stimulation with peptide, rhIL-2 was added to each well (10 IU/mL). One week later, the stimulated CD4$^+$ T-cells in each well were analyzed for specificity in IFN-gamma ELISPOT assays. The T-cells showing a specific response to the cognate peptide were transferred to 24-well plates and restimulated at weekly intervals with irradiated autologous PBMCs ($1 \times 10^6$ cells/well) pulsed with the peptide in medium supplemented with rhIL-2 (20 IU/mL) and rhIL-7 (5 ng/mL). In some instances, T-cells were cloned by limiting dilution for further studies as described previously (Tabata H, et al., Hum Immunol 1998; 59:549-60).

TABLE 2

HLA-A, -DR, and -DP genotypes of healthy donors

| Donor ID | HLA-A genotype | HLA-DRB1 genotype | HLA-DPB1 genotype |
|---|---|---|---|
| HD1 | A*02:01/24:02 | DRB1*04:05/— | DPB1*05:01/— |
| HD2 | A*11:01/31:01 | DRB1*08:03/15:02 | DPB1*02:01/09:01 |
| HD3 | A*24:02/31:01 | DRB1*08:03/14:05 | DPB1*02:02/05:01 |
| HD4 | A*02:01/02:06 | DRB1*09:01/04:05 | DPB1*02:01/04:02 |

HLA, human histocompatibility leukocyte antigen; n.t., not tested

Assessment of T-Cell Responses to Peptides and Proteins

The immune response of Th cells to antigen-presenting cells (APCs) pulsed with peptides or proteins was assessed by IFN-gamma enzyme-linked immunospot (ELISPOT) assays (BD Biosciences) as described previously (Tomita Y, et al., Cancer Sci 2011; 102:697-705). Briefly, the frequency of peptide-specific CD4$^+$ T-cells producing IFN-gamma per $3 \times 10^4$ bulk CD4$^+$ T-cells upon stimulation with peptide-pulsed PBMCs ($3 \times 10^4$ cells/well), or $1 \times 10^4$ bulk CD4$^+$ T-cells upon stimulation with peptide-pulsed HLA-DR-expressing L-cells ($5 \times 10^4$ cells/well) was analyzed. To determine the restriction by HLA molecules involved in antigen presentation, blocking of antigen-induced IFN-gamma production was investigated by adding anti-HLA-DR monoclonal antibody (mAb) (L243, BioLegend), anti-HLA-DP mAb, (B7/21, Abcam), anti-human HLA-DQ mAb (SPV-L3, Abcam), or anti-HLA class I mAb, (W6/32, Abcam). All mAbs were used at a final concentration of 5 micro-g/mL. All assessments of IFN-gamma ELISPOT assays were carried out in triplicate or duplicate, and results are presented as means+/−SD.

Cytokine Assays

HLA-DR-restricted IMP-3$_{507\text{-}527}$-LP-specific bulk Th cells and the Th cell clones (Th-clone, 1×10$^4$ cells/well) were cultured with autologous PBMCs (3×10$^4$ cells/well) in the presence of cognate peptide in 96-well culture plates. After 24 h, culture supernatants were collected and cytokine (IL-2, IFN-gamma, GM-CSF, TNF-alpha, IL-4 and IL-17) levels were measured using the Bio-Plex system (Bio-Rad) according to manufacturer's instructions.

CD107a Mobilization Assay

To identify degranulating CD4$^+$ T lymphocytes stimulated by the peptides, CD107a on the cell surface was analyzed by flow cytometry (Rubio V, et al., Nat Med 2003; 9:1377-82; Betts M R, et al., J Immunol Methods 2003; 281:65-78). In brief, a CD107a mobilization assay was performed as described previously (Tomita Y, et al., Cancer Sci 2011; 102:71-8). The cognate-LP or control LP (1 micro-g/mL) were added as stimulants, and FITC-labeled anti-human CD107a mAb or FITC-labeled isotype control mouse IgG1 and monensin were added to each well. Cells were cultured for 5 h at 37 degrees C. After culture, the peptide-stimulated Th cells were stained with PE-conjugated anti-human CD4 antibody (eBioscience, San Diego, Calif.) and analyzed on a FACScan (BD Bioscience, Bedford, Mass.) flow cytometer.

In Vitro Cross-Priming Assay

The peripheral monocyte-derived dendritic cells (DC) were generated as previously described. The DCs were pulsed with 20 micro-g/mL of the IMP-3$_{507\text{-}527}$-LP for 3 h. The cells were then irradiated (45 Gy) and incubated with the isolated CD8$^+$ T cells on day 0. Two additional stimulations with peptide-loaded autologous DCs were performed on days 7 and 14. Six days after the last stimulation, the number of IFN-gamma producing CD8$^+$ T-cells (1×10$^5$ cells/well) upon stimulation with IMP-3-A2$_{515\text{-}523}$SP-pulsed T2 cells (2×10$^4$ cells/well) was counted by ELISPOT assay.

In Vivo Cross-Priming Assay

HLA-A2 (HHD) transgenic mice (Tgm) were kindly provided by Dr. F. A. Lemonnier (Firat H, et al., Eur J Immunol 1999; 29:3112-21; Jung K O, et al., J Virol 2012; 86:7616-24). Mice were intradermally injected at the base of the tail with IMP-3$_{507\text{-}527}$-LP solution (HLA-A2 Tgm, 100 micro-g/mouse) emulsified in incomplete Freund's adjuvant (IFA) at 7-day intervals. Seven days after the second vaccination with IMP-3$_{507\text{-}527}$-LP, CD8$^+$ T-cells were isolated from inguinal lymph nodes by positive selection with magnetic microbeads (Miltenyi Biotec, Auburn, Calif., USA). The number of IFN-gamma producing CD8$^+$ T-cells (1×10$^5$ cells/well) upon stimulation with IMP-3-A2$_{515\text{-}523}$SP-pulsed bone marrow-derived DCs (BM-DCs, 2×10$^4$ cells/well) was counted by ex vivo ELISPOT assay (Harao M, et al., Int J Cancer 2008; 123:2616-25; Inoue M, et al., Immunol Lett 2009; 126:67-72).

Statistical Analysis

The present inventors compared data by the two-tailed Student's t-test (bar graphs) or by the nonparametric Mann-Whitney U test (scatter-dot graph). Differences with a P value <0.05 were considered statistically significant for all tests.

Results

Prediction and Selection of Potential Promiscuous HLA Class II-Binding IMP-3 Long Peptides Containing CTL-Epitopes To identify potential promiscuous HLA-class II binding Th-cell epitopes of IMP-3, the present inventors first examined the amino acid sequence of IMP-3 using a recently developed computer algorithm (FIG. 1A and Table 1) (Wang P, et al., BMC Bioinformatics 2010; 11:568; Wang P, et al., PLoS Comput Biol 2008; 4:e1000048). One region, IMP-3$_{402\text{-}423}$-LP-peptide, was predicted to be a potent promiscuous HLA class II-binding peptide by the computer algorithm, although it does not include a known CTL-epitope sequence. Another region, IMP-3$_{507\text{-}527}$-LP, predicted to be a potent promiscuous HLA class II-binding peptide by the computer algorithm, was proximal to the CTL epitopes recognized by HLA-A2 or A24-restricted CTLs (FIG. 1B). Therefore, the present inventors synthesized 2 candidate LPs, IMP-3$_{402\text{-}423}$-LP and IMP-3$_{507\text{-}527}$-LP, predicted to have strong binding affinity to frequent HLA-class II molecules in the Japanese population, HLA-DR9, HLA-DR4 and HLA-DR15, and one of them includes 9-mer peptides recognized by HLA-A2- or -A24-restricted CTLs for subsequent analyses.

Identification of Promiscuous IMP-3-Derived Th-Cell

CD4$^+$ T-cells isolated from PBMCs of healthy donors were stimulated at weekly intervals with autologous DCs and PBMCs pulsed with IMP-3$_{402\text{-}423}$-LP. After at least 3 rounds of stimulations, IMP-3$_{402\text{-}423}$-LP-specific responses of cultured CD4$^+$ T-cells were examined by IFN-gamma ELISPOT assays. In an HLA-DR53-positive healthy donor (HD1), the generated Th cells produced a significant amount of IFN-gamma in response to IMP-3$_{402\text{-}423}$-LP-pulsed PBMCs in an HLA-DR-dependent manner. The bulk Th cells specifically recognized L-DR53 cells pulsed with IMP-3$_{402\text{-}423}$-LP in an HLA-DR-dependent manner, but not unpulsed L-DR53 cells or IMP-3$_{402\text{-}423}$-LP-pulsed L-DR4 cells (FIG. 2A). These results indicated that IMP-3$_{402\text{-}423}$-LP was presented by HLA-DR53. To investigate whether IMP-3$_{402\text{-}423}$-LP induces responses in Th cells restricted by other HLA class II molecules, CD4$^+$ T-cells from other healthy donors were tested. The present inventors confirmed IMP-3$_{402\text{-}423}$-LP generates HLA-DR8 (DRB1*08:03)-restricted Th cells and HLA-DR (DRB1*08:03 or 14:05)-restricted bulk Th cells (FIGS. 2B and C). Thus, IMP-3$_{402\text{-}423}$-LP binds to HLA-DR53, HLA-DR8 and the other HLA-DR molecule, suggesting IMP-3$_{402\text{-}423}$-LP is a promiscuous Th-cell epitope presented by frequent HLA class II molecules (Saito S, et al., Tissue Antigens 2000; 56:522-9; Mack S J, et al., Tissue Antigens 2000; 55:383-400).

Next, the present inventors assessed whether IMP-3$_{507\text{-}527}$-LP, which bears a known CTL-epitope, can generate Th cells. In an HLA-DR8 and DR14-positive healthy donor (HD3), the generated Th cells produced a significant amount of IFN-gamma in response to IMP-3$_{507\text{-}527}$-LP-pulsed PBMCs in an HLA-DR-dependent manner (FIG. 2D). To investigate whether IMP-3$_{507\text{-}527}$-LP can induce responses in Th cells restricted by other HLA class II molecules, CD4$^+$ T-cells from an HLA-DR8 and DR14-negative healthy donor (HD4) were tested. The present inventors confirmed that IMP-3$_{507\text{-}527}$-LP could generate HLA-DR9-restricted bulk Th cells in this donor (FIG. 2E). These results demonstrate IMP-3$_{507\text{-}527}$-LP is also a promiscuous Th-cell epitope.

IMP-3$_{507-527}$-LP are Naturally Processed and Presented by DCs

The present inventors proceeded to assess whether DCs take up and process the IMP-3 protein to stimulate IMP-3-specific Th-clones. DCs loaded with recombinant IMP-3 protein were prepared and used as APCs in IFN-gamma ELISPOT assays (Tomita Y, et al., Cancer Sci 2011; 102: 71-8; Harao M, et al., Int J Cancer 2008; 123:2616-25). An HLA-DR9-restricted IMP-3$_{507-527}$-LP-reactive Th-clone efficiently recognized DCs loaded with IMP-3 protein, but did not recognize control protein-loaded DCs, indicating this epitope was naturally processed and presented by HLA-DR9 molecules (FIG. 3A). An HLA-DR53-restricted IMP-3$_{402-423}$-LP-reactive Th-clone efficiently recognized DCs loaded with IMP-3 protein in an HLA-DR-dependent manner, but did not recognize control protein-loaded DCs, indicating that this epitopes was also naturally processed and presented by HLA-DR53 molecules (FIG. 3B). In summary, the results indicate IMP-3$_{402-423}$-LP and IMP-3$_{507-527}$-LP are naturally processed from IMP-3 protein and presented by DCs.

IMP-3$_{507-527}$-LP Stimulates Th1-Type CD4$^+$ T-Cells

In order to further characterize IMP-3-LP-reactive Th cells, the present inventors used the Bio-Plex system to measure the levels of several cytokines released in response to stimulation by the cognate peptide. IMP-3$_{507-527}$-LP-specific bulk Th cells from HD3 produced a large amount of IFN-gamma, TNF-alpha, IL-2, and GM-CSF, but less IL-4 and IL-17 after restimulation with cognate peptide, indicating Th1-polarized characteristics (FIG. 4A). The cytotoxicity marker CD107a was also detected on the IMP-3$_{402-423}$-LP-specific and IMP-3$_{507-527}$-LP-specific bulk Th cells stimulated with cognate peptide (FIG. 4B), as was previously demonstrated for antiviral CD4$^+$ effector T cells and tumor-infiltrating CD4$^+$ lymphocytes (Casazza J P, et al., J Exp Med 2006; 203:2865-77; Attig S, et al., Cancer Res 2009; 69:8412-9; Widenmeyer M, et al., Int J Cancer 2012; 131:140-9; Martorelli D, et al., Int Rev Immunol 2010; 29:371-402). These data suggest that IMP-3-specific Th cells provide not only a helper function but also direct cytotoxic activity, both of which are advantageous for cancer immunotherapy.

Cross-Presentation of IMP-3-LPs Efficiently Primes IMP-3-Specific CD8$^+$ T-Cells In Vitro and In Vivo To assess the capacity of IMP-3$_{507-527}$-LP to induce IMP-3-A2$_{515-523}$-specific CTLs in vitro, CD8$^+$ T cells isolated from PBMCs of healthy donors were stimulated at weekly intervals with IMP-3$_{507-527}$-LP-pulsed autologous DCs. After at least 3 rounds of stimulations, the CD8$^+$ T-cells produced larger amount of IFN-gamma in response to IMP-3$_{515-523}$-SP-pulsed T2 cells in HLA-A2-positive healthy donors (HD1 and HD4) (FIG. 5A).

The capacity of IMP-3$_{507-527}$-LP to prime IMP-3-A2$_{515-523}$-specific CTLs was examined by an ex vivo IFN-gamma ELISPOT assay. HLA-A2 Tgm were immunized 2 times with IMP-3$_{507-527}$-LP emulsified in IFA. The CD8$^+$ T-cells of HLA-A2 Tgm vaccinated with IMP-3$_{507-527}$-LP produced IFN-gamma specifically in response to stimulation with BM-DCs pulsed with the IMP-3-A2$_{515-523}$ SP (FIG. 5B). These results suggested that after uptake of IMP-3$_{507-527}$-LP, APCs can cross-prime IMP-3-A2$_{515-523}$ SP-specific CTL in vivo in HLA-A2 Tgm.

DISCUSSION

Several phase I/II clinical trials using IMP-3-A2$_{515-523}$ SP and IMP-3-A24$_{508-516}$ SP against different types of tumor are ongoing (Mizukami Y, et al., Cancer Sci 2008; 99:1448-54; Kono K, et al., Cancer Sci 2009; 100:1502-9; Kono K, et al., J Transl Med 2012; 10:141). The results of these trials are promising in some advanced cancer patients. Therefore, the present inventors attempted to identify the LPs that induce both antigen-specific Th1 cells and CTLs in order to further develop peptide vaccine immunotherapy.

The present inventors identified two promiscuous IMP-3-derived Th cell epitope peptides. One of them includes both HLA-A2 and -A24-restricted CTL-epitopes. The present inventors confirmed IMP-3$_{402-423}$-LP and IMP-3$_{507-527}$-LP were naturally processed and presented on cell surfaces in the context of HLA class II molecule. The present inventors also demonstrated that IMP-3$_{507-527}$-LP-specific CD4$^+$ T-cells had Th1-polarized characteristics, suggesting that the CD4$^+$ T-cells induced by IMP-3-LPs have the advantageous characteristic for cancer immunotherapy.

IMP-3-LPs induced HLA-DR9, DR8, and DR53-restricted Th cells. Further, IMP-3-LPs were suggested to have a possibility to induce HLA-DR14-restricted Th cells. HLA-DR9, DR8, DR14 and DR53 alleles are very frequent HLA class II molecules in Japanese and Pacific/Asian populations, and HLA-A2 and A24 alleles are also observed at high frequencies in those populations. In addition, IMP-3$_{507-527}$-LP induced priming and expansion of IMP-3-A2$_{515-523}$-specific CTLs in vitro and in vivo, suggesting that IMP-3-LP bearing IMP-3-SP epitopes can induce both IMP-3-specific Th cells and CTLs. Therefore, the present inventors believe that these immunogenic IMP-3-LPs could have the potential for inducing stronger anti-tumor responses.

Recent studies of LPs have shown that vaccines containing natural CTL-epitopes are superior to those composed of minimal CTL-epitopes in inducing anti-tumor CTL immunity because of long-lasting cross-presentation of the LPs (Melief C J, et al., Nat Rev Cancer 2008; 8:351-60; Bijker M S, et al., Eur J Immunol 2008; 38:1033-42; Chauvin J M, et al., J Immunol 2012; 188:2102-10). The present inventors have not yet compared the capacity to induce IMP-3-A2$_{515-523}$-specific CTLs between IMP-3$_{507-527}$-LP and IMP-3-A2$_{515-523}$ SP. This will be evaluated in a future study.

In conclusion, the present inventors identified two immunogenic IMP-3-LPs that can induce Th cells. One of them encompasses both IMP-3-A2 and IMP-3-A24 epitopes. Our results suggest that IMP-3-LPs provide a useful tool for propagation of both IMP-3-specific Th1 cells and CTLs. These findings support a possible clinical trial of IMP-3 peptide-based immunotherapy for various types of cancers.

INDUSTRIAL APPLICABILITY

The present invention describes Th1 cell epitope peptides derived from IMP-3 that can induce potent anti-tumor immune responses and thus have applicability to a wide array of cancer types. Such peptides warrant further development as peptide vaccines against cancer, especially against cancers expressing IMP-3. The peptides of the present invention can induce the Th1 cell response and thus cytokines secreted by Th1 cells can help or activate any immune cells responsible for cellular immunity in an antigen independent manner. Therefore, immunotherapeutic strategy provided by the present invention can be applied to any diseases including cancers, as long as the disease can be improved via immune responses mediated by MHC class II molecules. In particular, Th1 cells of the present invention can improve immunological responses raised by CTLs. Therefore, the peptide of the present invention would be beneficial to enhance CTL response against diseases including cancers in a subject.

Moreover, in preferred embodiments, the peptides of the present invention can also induce CTLs against IMP-3 expressing cells, as well as Th1 cells. Such peptide of the present invention can be also useful for the treatment of diseases associated with IMP-3, e.g. cancers, more particularly, bladder cancer, cervical cancer, cholangiocellular carcinoma, chronic myelocytic leukemia, colon cancer, rectum cancer, esophageal cancer, gastric diffuse-type cancer, non-small-cell lung cancer (NSCLC), small-cell lung cancer (SCLC), lymphoma, osteosarcoma, ovarian cancer, renal carcinoma, soft tissue tumor, testicular tumor, and HNC.

While the present invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention, the metes and bounds of which are defined by the appended claims.

The invention claimed is:

1. An isolated peptide consisting the amino acid sequence of SEQ ID NO: 2 in which one amino acid is substituted, wherein said peptide has ability to induce T helper type 1 (Th1) cells.

2. The isolated peptide of claim 1, wherein the peptide has abilities to bind at least two kinds of MHC class II molecules.

3. The isolated peptide of claim 2, wherein the MHC class II molecules are selected from the group consisting of HLA-DR8, HLA-DR53, HLA-DR14, and HLA-DR9.

4. The isolated peptide of claim 1, wherein said peptide comprises an amino acid sequence of a peptide having IMP-3-specific cytotoxic T lymphocyte (CTL) inducibility.

5. A composition comprising one or more peptide(s) consisting of 10-30 amino acids in length and comprising a part of the amino acid sequence of SEQ ID NO: 6, wherein said peptide comprises an amino acid sequence selected from the group consisting of:
   (a) a contiguous amino acid sequence having more than 9 amino acids in length selected from the amino acid sequence of SEQ ID NO: 2, and
   (b) the amino acid sequence of SEP ID NO: 2 in which one or two amino acids are substituted, deleted, inserted, and/or added
   in combination with an adjuvant in an amount effective to enhance an immune response,
   wherein said composition further comprises one or more peptides having CTL inducibility.

6. A method for inducing an APC having an ability to induce a Th1 cell, said method comprising a step of contacting an APC with the peptide of claim 1 in vitro, ex vivo or in vivo.

7. A method for inducing an APC having an ability to induce a CTL, said method comprising a step contacting an APC with the peptide of claim 1 in vitro, ex vivo or in vivo.

8. A method for inducing a Th1 cell, said method comprising a step co-culturing a CD4-positive T cell with an APC that presents on its surface a complex of an MHC class II molecule and the peptide of claim 1.

9. A method for inducing a CTL, said method comprising the step selected from the group consisting of:
   (a) co-culturing both of a CD4-positive T cell and a CD8-positive T cell with APCs contacted with the peptide of claim 4; and
   (b) co-culturing a CD8-positive T cell with an APC contacted with the peptide of claim 4.

10. A method for enhancing an immune response mediated by an MHC class II molecule, wherein the method comprises a step of administering to one or more peptide(s) of claim 1.

11. A method of inducing an immune response against cancer in a subject in need thereof, said method comprising the step of administering to the subject a composition comprising one or more peptide(s) of claim 1.

12. The composition of claim 5, wherein the peptide(s) are selected from the group consisting of:
   (a) a peptide consisting of the amino acid sequence of SEQ ID NO: 2, and
   (b) a peptide consisting of the amino acid sequence of SEQ ID NO: 2 in which one or two amino acids are substituted, deleted, inserted, and/or added.

13. The composition of claim 12, wherein the peptide(s) consist of the amino acid sequence of SEQ ID NO: 2.

* * * * *